(12) United States Patent
Weber et al.

(10) Patent No.: US 9,844,460 B2
(45) Date of Patent: Dec. 19, 2017

(54) TREATMENT SYSTEMS WITH FLUID MIXING SYSTEMS AND FLUID-COOLED APPLICATORS AND METHODS OF USING THE SAME

(71) Applicant: Zeltiq Aesthetics, Inc., Pleasanton, CA (US)

(72) Inventors: Bryan J. Weber, Livermore, CA (US); Joseph Coakley, Dublin, CA (US); Mark William Baker, Livermore, CA (US); Thomas Burnell Reeve, III, San Francisco, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 745 days.

(21) Appl. No.: 13/830,027

(22) Filed: Mar. 14, 2013

(65) Prior Publication Data

US 2014/0277302 A1    Sep. 18, 2014

(51) Int. Cl.
*A61F 7/00* (2006.01)
*A61F 7/02* (2006.01)

(52) U.S. Cl.
CPC .... *A61F 7/0085* (2013.01); *A61F 2007/0054* (2013.01); *A61F 2007/0093* (2013.01); *A61F 2007/0095* (2013.01); *A61F 2007/029* (2013.01); *A61F 2007/0295* (2013.01)

(58) Field of Classification Search
CPC ............ A61F 7/0085; A61F 2007/0018; A61F 2007/0022–2007/27; A61F 2007/0054; A61F 2007/0056
See application file for complete search history.

(56) References Cited

U.S. PATENT DOCUMENTS

| | | |
|---|---|---|
| 681,806 A | 9/1901 | Mignault et al. |
| 2,889,810 A | 6/1908 | Robinson et al. |
| 2,516,491 A | 7/1950 | Swastek |

(Continued)

FOREIGN PATENT DOCUMENTS

| | | |
|---|---|---|
| AU | 2011253768 A1 | 6/2012 |
| CA | 2441489 A1 | 3/2005 |

(Continued)

OTHER PUBLICATIONS

"ThermaCool Monopolar Capacitive Radiofrequency, The one choice for nonablative tissue tightening and contouring", Thermage, Inc. Tech Brochure, Nov. 30, 2005, 8 pgs.

(Continued)

*Primary Examiner* — Ronald Hupczey, Jr.
(74) *Attorney, Agent, or Firm* — Perkins Coie LLP

(57) ABSTRACT

A treatment system for cooling subcutaneous lipid-rich cells in a human subject includes an applicator and a control unit. The treatment system has a cooling mode for cooling tissue and a heating mode for warming tissue. The control unit includes a circulation circuit in fluid communication with the applicator, a chiller apparatus configured to chill fluid from the applicator circulation circuit, and a heater apparatus to warmed fluid from the applicator circulation circuit. The control unit mixes the chilled fluid and/or the warmed with fluid in the applicator circulation circuit control the temperature of the fluid circulated in the applicator.

29 Claims, 14 Drawing Sheets

(56) References Cited

U.S. PATENT DOCUMENTS

| | | |
|---|---|---|
| 2,521,780 A | 9/1950 | Dodd et al. |
| 2,726,658 A | 12/1955 | Chessey |
| 2,766,619 A | 10/1956 | Tribus et al. |
| 2,851,602 A | 9/1958 | Cramwinckel et al. |
| 3,093,135 A | 6/1963 | Hirschhorn |
| 3,132,688 A | 5/1964 | Nowak |
| 3,133,539 A | 5/1964 | William et al. |
| 3,282,267 A | 11/1966 | Eidus |
| 3,502,080 A | 3/1970 | Hirschhorn |
| 3,587,577 A | 6/1971 | Zubkov et al. |
| 3,591,645 A | 7/1971 | Selwitz |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Andera et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,026,299 A | 5/1977 | Sauder |
| 4,140,130 A | 2/1979 | Storm |
| 4,149,529 A | 4/1979 | Copeland et al. |
| 4,178,429 A | 12/1979 | Scheffer |
| 4,202,336 A | 5/1980 | Van Gerven |
| 4,266,043 A | 5/1981 | Fujii et al. |
| 4,269,068 A | 5/1981 | Molina |
| 4,381,009 A | 4/1983 | Del Bon |
| 4,396,011 A | 8/1983 | Mack et al. |
| 4,459,854 A | 7/1984 | Richardson et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler et al. |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott et al. |
| 5,007,433 A | 4/1991 | Hermsdoerffer et al. |
| 5,018,521 A | 5/1991 | Campbell et al. |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney et al. |
| 5,327,886 A | 7/1994 | Chiu |
| 5,330,745 A | 7/1994 | Mcdow et al. |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold et al. |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan et al. |
| 5,433,717 A | 7/1995 | Rubinsky et al. |
| 5,456,703 A | 10/1995 | Beeuwkes, III et al. |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards et al. |
| 5,507,790 A | 4/1996 | Weiss |
| 5,514,105 A | 5/1996 | Goodman, Jr. et al. |
| 5,514,170 A | 5/1996 | Mauch |
| 5,516,505 A | 5/1996 | McDow |
| 5,531,742 A | 7/1996 | Barken |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay et al. |
| 5,660,836 A | 8/1997 | Knowlton et al. |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,736 A | 5/1998 | Tankovich |
| 5,755,663 A | 5/1998 | Larsen et al. |
| 5,755,753 A | 5/1998 | Knowlton et al. |
| 5,755,755 A | 5/1998 | Panyard |
| 5,759,182 A | 6/1998 | Varney et al. |
| 5,759,764 A | 6/1998 | Polovina et al. |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,814,040 A | 9/1998 | Nelson et al. |
| 5,817,050 A | 10/1998 | Klein et al. |
| 5,817,149 A | 10/1998 | Owens et al. |
| 5,817,150 A | 10/1998 | Owens et al. |
| 5,830,208 A | 11/1998 | Muller et al. |
| 5,833,685 A | 11/1998 | Tortal et al. |
| 5,844,013 A | 12/1998 | Kenndoff et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton et al. |
| 5,944,748 A | 8/1999 | Mager et al. |
| 5,948,011 A | 9/1999 | Knowlton et al. |
| 5,954,680 A | 9/1999 | Augustine et al. |
| 5,964,092 A | 10/1999 | Tozuka et al. |

(56) References Cited

U.S. PATENT DOCUMENTS

| | | |
|---|---|---|
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A | 11/2000 | Koby et al. |
| 6,152,952 A | 11/2000 | Owens et al. |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |

(56) References Cited

U.S. PATENT DOCUMENTS

| | | |
|---|---|---|
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey, Sr. et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith, III et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2005/0010197 A1 | 1/2005 | Lau et al. |
| 2005/0033957 A1 | 2/2005 | Enokida |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0277859 A1 | 12/2005 | Carlsmith et al. |

(56) References Cited

U.S. PATENT DOCUMENTS

| | | |
|---|---|---|
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0122509 A1 | 6/2006 | Desilets |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1* | 3/2008 | Levinson ............... A61F 7/10 607/96 |
| 2008/0077211 A1 | 3/2008 | Levinson et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0161892 A1 | 7/2008 | Mercuro et al. |
| 2008/0183164 A1 | 7/2008 | Elkins et al. |
| 2008/0188915 A1 | 8/2008 | Mills et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0276018 A1 | 11/2009 | Brader |
| 2009/0281464 A1 | 11/2009 | Cioanta et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0217349 A1 | 8/2010 | Fahey et al. |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |

(56) References Cited

U.S. PATENT DOCUMENTS

| | | |
|---|---|---|
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1* | 8/2014 | Spence ............... A41D 13/005 607/104 |
| 2014/0277219 A1 | 9/2014 | Nanda |
| 2014/0277302 A1 | 9/2014 | Weber et al. |
| 2014/0277303 A1 | 9/2014 | Biser et al. |
| 2014/0303697 A1 | 10/2014 | Anderson et al. |
| 2015/0209174 A1 | 7/2015 | Abreu |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0328077 A1 | 11/2015 | Levinson |
| 2015/0335468 A1* | 11/2015 | Rose .................... A61F 7/0085 607/104 |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0135985 A1 | 5/2016 | Anderson |
| 2016/0324684 A1 | 11/2016 | Levinson et al. |
| 2017/0165105 A1 | 6/2017 | Anderson et al. |
| 2017/0196731 A1 | 7/2017 | Debenedictis et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 532976 C | 9/1931 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 2260801 A2 | 12/2010 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 2120944 A | 12/1983 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 2000503154 A | 3/2000 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 12/1999 |
| KR | 1020040094508 A | 11/2004 |
| KR | 20090000258 U | 1/2009 |
| KR | 1020130043299 A | 4/2013 |
| KR | 1020140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |

(56) References Cited

FOREIGN PATENT DOCUMENTS

| | | |
|---|---|---|
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2014191263 A1 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.

Bohm, T. et al., "Saline-Enhanced Radiofrequency Ablation of Breast Tissue: an in Vitro Feasibility Study," Investigative Radiology, vol. 35 (3), 2000, pp. 149-157.

Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.

Burge, S. M. et al., "Hair Follicle Destruction and Regeneration in Guinea Pig Skin after Cutaneous Freeze Injury," Cryobiology, 27(2), 1990, pp. 153-163.

Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.

Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.

Donski, P. K. et al., "The Effects of Cooling no Experimental Free Flap Survival," British Journal of Plastic Surgery, vol. 33, 1980, pp. 353-360.

Duck, F. A., Physical Properties of Tissue, Academic Press Ltd., chapters 4 & 5, 1990, pp. 73-165.

Duncan, W. C. et al., "Cold Panniculitis," Archives of Dermatology, vol. 94, Issue 6, Dec. 1966, pp. 722-724.

Epstein, E. H. et al., "Popsicle Panniculitis," The New England Journal of Medicine, 282(17), Apr. 23, 1970, pp. 966-967.

Fournier, L. et al. "Lattice Model for the Kinetics of Rupture of Fluid Bilayer Membranes," Physical Review, vol. 67, 2003, pp. 051908-1-051908-11.

Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.

Gage, A. "Current Progress in Cryosurgery," Cryobiology 25, 1988, pp. 483-486.

Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].

Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.

Heller Page, E. et al., "Temperature-dependent skin disorders," Journal of the American Academy of Dermatology, vol. 18, No. 5, Pt 1, May 1988, pp. 1003-1019.

Hemmingsson, A. et al. "Attenuation in Human Muscle and Fat Tissue in Vivo and in Vitro," Acra Radiologica Diagnosis, vol. 23, No. 2, 1982, pp. 149-151.

Henry, F. et al., "Les Dermatoses Hivernales," Rev Med Liege, 54:11, 1999, pp. 864-866. [Abstract Attached].

Hernan, P. et al., "Study for the evaluation of the efficacy of Lipocryolysis (EEEL)", Nov. 30, 2011.

Hernan, R. P., "A Study to Evaluate the Action of Lipocryolysis", 33(3) CryoLellers, 2012, pp. 176-180.

Holland, DB. et al. "Cold shock induces the synthesis of stress proteins in human keratinocytes," PubMed Journal of Investigative Dermatology; 101(2): Aug. 1993, pp. 196-199.

Holman, W. L. et al., "Variation in Cryolesion Penetration Due to Probe Size and Tissue Thermal Conductivity," The Annals of Thoracic Surgery, vol. 53, 1992, pp. 123-126.

Hong, J.S. et al., "Patterns of Ice Formation in Normal and Malignant Breast Tissue," Cryobiology 31, 1994, pp. 109-120.

(56) References Cited

OTHER PUBLICATIONS

Huang et al. "Comparative Proteomic Profiling of Murine Skin," Journal of Investigative Dermatology, vol. 121(1), Jul. 2003, pp. 51-64.
International Report on Patentability for PCT/US2014/026596 dated Sep. 24, 2015, 11 pages.
International Search Report and Written Opinion for PCT/US2014/026596; dated Nov. 10, 2014, 16 pages.
Isambert, H. "Understanding the Electroporation of Cells and Artificial Bilayer Membranes," Physical Review Letters, vol. 80, No. 15, 1998, pp. 3404-3707.
Jalian, H. R. et al., "Cryolipolysis: A Historical Perspective and Current Clinical Practice", 32(1) Semin. Cutan. Med. Surg., 2013, pp. 31-34.
Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.
Koska, J. et al., "Endocrine Regulation of Subcutaneous Fat Metabolism During Cold Exposure in Humans," Annals of the New York Academy of Sciences, vol. 967, 2002,pp. 500-505.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.
Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.
Levchenko et al., "Effect of Dehydration on Lipid Metabolism" Ukrainskii Biokhimicheskii Zhurnal, vol. 50, Issue 1, 1978, pp. 95-97.
Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.
Liu, A. Y.-C. et al., "Transient Cold Shock Induces the Heat Shock Response upon Recovery at 37 C in Human Cells," Journal of Biological Chemistry, , 269(20), May 20, 1994, pp. 14768-14775.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.
Maize, J.C. "Panniculitis," Cutaneous Pathology, Chapter 13, 1998, 327-344.
Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-invasive, Selective Lipolysis," Lasers Surg. Med 40:S20, 2008, p. 104.
Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: the Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.
Murphy, J. V. et al., "Frostbite: Pathogenesis and Treatment" The Journal of Trauma: Injury, Infection, and Critical Care, vol. 48, No. 1, Jan. 2000, pp. 171-178.
Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.
Nagle, W. A. et al. "Cultured Chinese Hamster Cells Undergo Apoptosis After Exposure to Cold but Nonfreezing Temperatures," Cryobiology 27, 1990, pp. 439-451.
Nagore, E. et al., "Lipoatrophia Semicircularis-a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.
Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Supplementum, vol. 323 (Copenhagen 1969), pp. 7-74.
Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.
Nurnberger, F. "So-Called Cellulite: An Invented Disease," Journal of Dermatologic Surgery and Oncology, Mar. 1978, pp. 221-229.
Pease, G. R. et al., "An Integrated Probe for Magnetic Resonance Imaging Monitored Skin Cryosurgery," Journal of Biomedical Engineering, vol. 117, Feb. 1995, pp. 59-63.
Pech, P. et al., "Attenuation Values, Volume Changes and Artifacts in Tissue Due to Freezing," Acta Radiologica ,vol. 28, Issue 6, 1987, pp. 779-782.
Peterson, L. J. et al., "Bilateral Fat Necrosis of the Scrotum," Journal of Urology, vol. 116, 1976, pp. 825-826.
Phinney, S. D. et al., "Human Subcutaneous Adipose Tissue Shows Site-Specific Differences in Fatty Acid Composition," The American Journal of Clinical Nutrition, vol. 60, 1994, pp. 725-729.
Pierard, G. E. et al., "Cellulite: From Standing Fat Herniation to Hypodermal Stretch Marks," The American Journal of Dermatology, vol. 22, Issue 1, 2000, pp. 34-37, [Abstract].
Pope, K. et al. "Selective Fibrous Septae Heating: An Additional Mechanism of Action for Capacitively Coupled Monopolar Radiofrequency" Thermage, Inc. Article, Feb. 2005, 6pgs.
Quinn, P. J. "A Lipid-Phase Separation Model of Low-Temperature Damage to Biological Membranes," Cryobiology, 22, 1985, 128-146.
Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.
Renold, A. E. et al. "Adipose Tissue" in Handbook of Physiology, Chapter 15, (Washington, D.C., 1965) pp. 169-176.
Rossi, A. B. R. et al. "Cellulite: a Review," European Academy of Dermatology and Venercology, 2000, pp. 251-262, 12 pgs.
Rubinsky, B. "Principles of Low Temperature Cell Preservation," Heart Failure Reviews, vol. 8, 2003, pp. 277-284.
Rubinsky, B. et al., "Cryosurgery: Advances in the Application of low Temperatures to Medicine," International Journal of Refrigeration, vol. 14, Jul. 1991, pp. 190-199.
Saleh, K. Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.
Schoning, P. et al., "Experimental Frostbite: Freezing Times, Rewarming Times, and Lowest Temperatures of Pig Skin Exposed to Chilled Air," Cryobiology 27, 1990, pp. 189-193.
Shephard, R. J. "Adaptation to Exercise in the Cold," Sports Medicine, vol. 2, 1985, pp. 59-71.
Sigma-Aldrich "Poly(ethylene glycol) and Poly(ethylene oxide)," http://www.sigmaaldrich.com/materials-science/materialscience-;products.htmi?TablePage=2020411 0, accessed Oct. 19, 2012.

(56) References Cited

OTHER PUBLICATIONS

Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.

Thermage, News Release, "Study Published in Facial Plastic Surgery Journal Finds Selective Heating of Fibrous Septae Key to Success and Safety of Thermage ThermaCool System," Jun. 20, 2005, 2 pages.

Vallerand et al. "Cold Stress Increases Lipolysis, FFA Ra and TG/FFA Cycling in Humans," Aviation, Space, and Environmental Medicine 70(1), 1999, pp. 42-50.

Wang, X. et al., "Cryopreservation of Cell/Hydrogel Constructs Based on a new Cell-Assembling Technique," Sep. 5, 2009, 40 pages.

Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.

Winkler, C. et al., "Gene Transfer in Laboratory Fish: Model Organisms for the Analysis of Gene Function," in Transgenic Animals, Generation and Use (The Netherlands 1997), pp. 387-395.

Young, H. E. et al. "Isolation of Embryonic Chick Myosatellite and Pluripotent Stem Cells" The Journal of Tissue Culture Methods, vol. 14, Issue 2, 1992, pp. 85-92.

Zelickson, B. et al., "Cryolipolysis for Noninvasive Fat Cell Destruction: Initial Results from a Pig Model", 35 Dermatol. Sug., 2009, pp. 1-9.

Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.

\* cited by examiner

TREATMENT SYSTEMS WITH FLUID MIXING SYSTEMS AND FLUID-COOLED APPLICATORS AND METHODS OF USING THE SAME

INCORPORATION BY REFERENCE OF COMMONLY-OWNED APPLICATIONS AND PATENTS

The following commonly assigned U.S. Patent Applications and U.S. Patents are incorporated herein by reference in their entirety:

U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Pat. No. 7,854,754 entitled "COOLING DEVICE FOR REMOVING HEAT FROM SUBCUTANEOUS LIPID-RICH CELLS";

U.S. Patent Publication No. 2011/0066216 entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE";

U.S. Patent Publication No. 2009/0118722, filed Oct. 31, 2007, entitled "METHOD AND APPARATUS FOR COOLING SUBCUTANEOUS LIPID-RICH CELLS OR TISSUE";

U.S. Patent Publication No. 2009/0018624 entitled "LIMITING USE OF DISPOSABLE SUBJECT 11 PROTECTION DEVICES";

U.S. Patent Publication No. 2009/0018623 entitled "SYSTEM FOR TREATING LIPID-RICH REGIONS";

U.S. Patent Publication No. 2009/0018625 entitled "MANAGING SYSTEM TEMPERATURE TO REMOVE HEAT FROM LIPID-RICH REGIONS";

U.S. Patent Publication No. 2009/0018627 entitled "SECURE SYSTEM FOR REMOVING HEAT FROM LIPID-RICH REGIONS";

U.S. Patent Publication No. 2009/0018626 entitled "USER INTERFACES FOR A SYSTEM THAT REMOVES HEAT FROM LIPID-RICH REGIONS";

U.S. Pat. No. 6,041,787 entitled "USE OF CRYOPROTECTIVE AGENT COMPOUNDS DURING CRYOSURGERY";

U.S. Pat. No. 8,285,390 entitled "MONITORING THE COOLING OF SUBCUTANEOUS LIPID-RICH CELLS, SUCH AS THE COOLING OF ADIPOSE TISSUE";

U.S. Provisional Patent Application Ser. No. 60/941,567 entitled "METHODS, APPARATUSES AND SYSTEMS FOR COOLING THE SKIN AND SUBCUTANEOUS TISSUE";

U.S. Pat. No. 8,275,442 entitled "TREATMENT PLANNING SYSTEMS AND METHODS FOR BODY CONTOURING APPLICATIONS";

U.S. patent application Ser. No. 12/275,002 entitled "APPARATUS WITH HYDROPHILIC RESERVOIRS FOR COOLING SUBCUTANEOUS LIPID-RICH CELLS";

U.S. patent application Ser. No. 12/275,014 entitled "APPARATUS WITH HYDROPHOBIC FILTERS FOR REMOVING HEAT FROM SUBCUTANEOUS LIPID-RICH CELLS";

U.S. Patent Publication No. 2010/0152824 entitled "SYSTEMS AND METHODS WITH INTERRUPT/RESUME CAPABILITIES FOR COOLING SUBCUTANEOUS LIPID-RICH CELLS";

U.S. Patent Publication No. 2008/0077202 entitled "TISSUE TREATMENT METHODS";

U.S. Patent Publication No. 2010/0280582 entitled "DEVICE, SYSTEM AND METHOD FOR REMOVING HEAT FROM SUBCUTANEOUS LIPID-RICH CELLS";

U.S. Patent Publication No. 2012/0022518 entitled "COMBINED MODALITY TREATMENT SYSTEMS, METHODS AND APPARATUS FOR BODY CONTOURING APPLICATIONS";

U.S. Publication No. 2011/0238050 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2011/0238051 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2012/0239123 entitled "DEVICES, APPLICATION SYSTEMS AND METHODS WITH LOCALIZED HEAT FLUX ZONES FOR REMOVING HEAT FROM SUBCUTANEOUS LIPID-RICH CELLS"; and U.S. Pat. No. 9,545,523 entitled "MULTI-MODALITY TREATMENT SYSTEMS, METHODS AND APPARATUS FOR ALTERING SUBCUTANEOUS LIPID-RICH TISSUE".

TECHNICAL FIELD

The present application relates generally to treatment systems and methods for non-invasively heating and cooling subcutaneous tissue. In particular, several embodiments are directed to fluid mixing systems and methods for controlling the temperature of fluids delivered to fluid-cooled applicators to cool subcutaneous lipid-rich cells.

BACKGROUND

Excess body fat, or adipose tissue, may be present in various locations of the body, including, for example, the thighs, buttocks, abdomen, knees, back, face, arms, chin, and other areas. Moreover, excess adipose tissue is thought to magnify the unattractive appearance of cellulite, which forms when subcutaneous fat protrudes into the dermis and creates dimples where the skin is attached to underlying structural fibrous strands. Cellulite and excessive amounts of adipose tissue are often considered to be unappealing. Moreover, significant health risks may be associated with higher amounts of excess body fat.

A variety of methods have been used to treat individuals having excess body fat and, in many instances, non-invasive removal of excess subcutaneous adipose tissue can eliminate unnecessary recovery time and discomfort associated with invasive procedures such as liposuction. Conventional non-invasive treatments for removing excess body fat typically include topical agents, weight-loss drugs, regular exercise, dieting or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or other negative reaction. Furthermore, fat loss in selective areas of a person's body often cannot be achieved using general or systemic weight-loss methods.

BRIEF DESCRIPTION OF THE DRAWINGS

Non-limiting and non-exhaustive embodiments are described with reference to the following drawings. Many features of the present technology are illustrated in simplified, schematic, and/or partially schematic formats in the following Figures to avoid obscuring significant technology features. The same reference numerals refer to like parts or acts throughout the various views, unless otherwise specified.

DETAILED DESCRIPTION OF TECHNOLOGY

1. Overview

Figure 1:
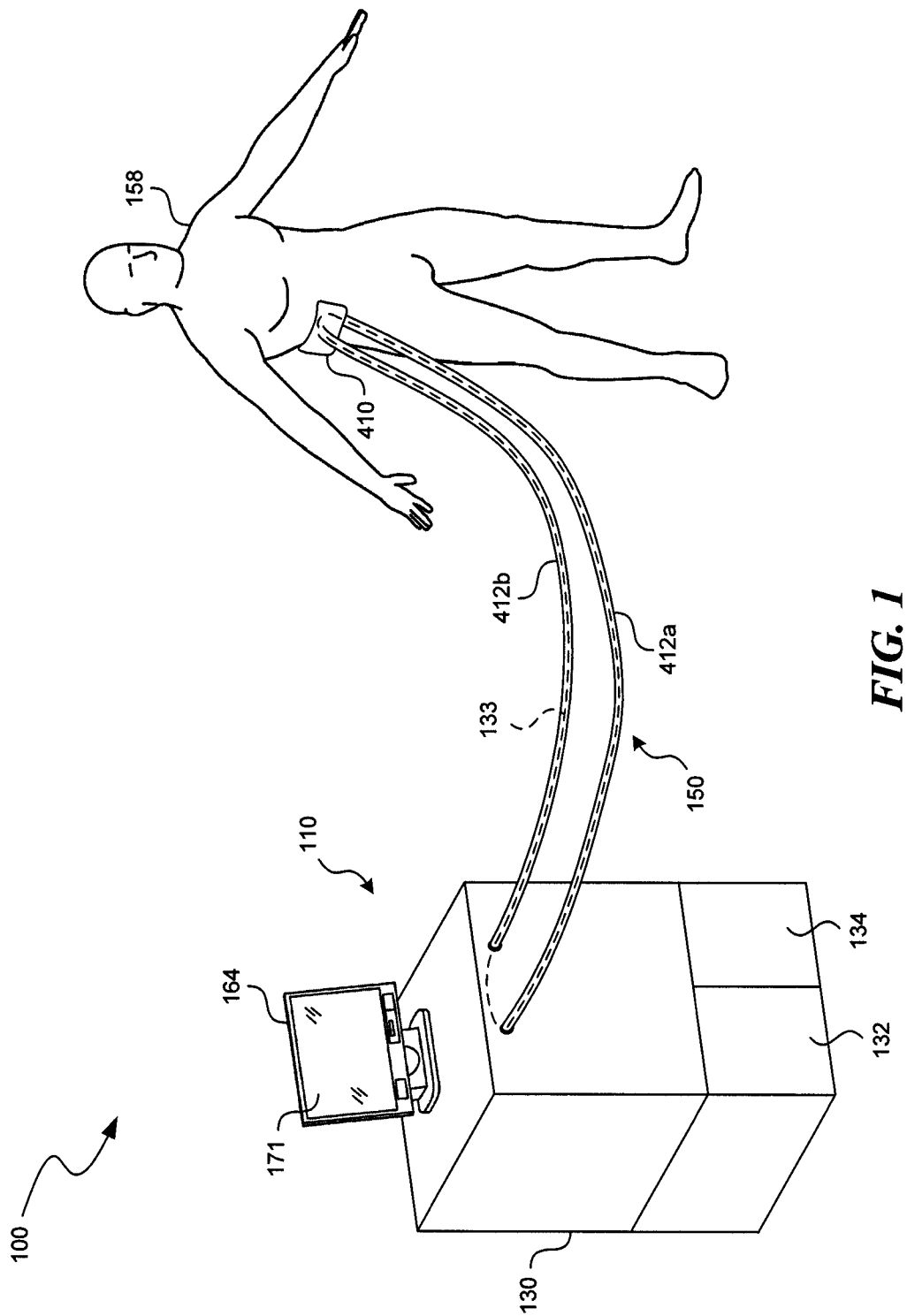
FIG. 1 is a schematic illustration of a treatment system for treating a target region of a subject in accordance with one embodiment.

Several examples of systems, devices, and methods for controlling the temperature of a subject's tissue in accordance with the presently disclosed technology are described below. Although the following description provides many specific details of the following examples in a manner sufficient to enable a person skilled in the relevant art to practice, make and use them, several of the details and advantages described below may not be necessary to practice certain examples and methods of the technology. Additionally, the technology may include other examples and methods that are within the scope of the claims but are not described here in detail.

At least some embodiments are directed to a treatment system for cooling subcutaneous tissue. The treatment system can include a fluid mixing system capable of controlling the temperature of coolant delivered to an applicator which absorbs heat from the subcutaneous tissue. In some embodiments, the absorbed heat is transferred to coolant circulating within the applicator. The treatment system can hold coolants at different temperatures to achieve a wide range of temperature profiles. In some embodiments, the fluid mixing system can use a volume of pre-cooled coolant (e.g., a temperature lower than a treatment temperature) to reduce the temperature of circulating coolant delivered to the applicator.

In some embodiments, a treatment system includes a mixing or circulation reservoir for holding a volume of heat transfer fluid. Chilled heat transfer fluid can be delivered into the mixing reservoir to reduce the average temperature of the heat transfer fluid in the mixing reservoir. The cooled heat transfer fluid from the mixing reservoir can be delivered to an applicator. In other embodiments, the treatment system can include a mixing conduit in which warm heat transfer fluid (i.e., heat transfer fluid at a higher than the temperature of the chilled heat transfer fluid) can be mixed with chilled heat transfer fluid to obtain cooled heat transfer fluid. For example, the cooled heat transfer fluid can be directly delivered into a stream of warm heat transfer fluid flowing through the mixing conduit.

In some embodiments, a circulation circuit includes a delivery conduit that delivers coolant from a mixing reservoir to an applicator. A return conduit can deliver warmed coolant (e.g., coolant that has absorbed heat from the subject) from the applicator to the mixing reservoir. In one mode of operation, chilled or cold coolant from a chilled coolant reservoir can be delivered into the applicator circulation circuit to reduce the temperature of the coolant delivered to the applicator. In another mode of operation, heated coolant from a heated coolant reservoir can be delivered into the applicator circulation circuit to raise the temperature of the coolant delivered to the applicator. Example coolants include, without limitation, water, glycol, synthetic heat transfer fluids, oil, refrigerants, and/or any other suitable heat conducting fluid.

In some embodiments, a mixing reservoir and a chilled coolant reservoir have a common wall. The wall can limit or reduce heat absorption by the mixing reservoir and/or chilled coolant reservoir. Additionally or alternatively, at least a portion of the mixing reservoir can be positioned within a chamber of the chilled coolant reservoir. When the chilled coolant reservoir is filled with coolant, at least a portion of the mixing reservoir can be in contact with the chilled coolant. For example, a bottom portion of the mixing reservoir can be immersed in the chilled coolant. Such embodiments can reduce a length of the flow path between the mixing reservoir and the chilled coolant reservoir. This reduced flow path can limit or reduce the flow resistance to enhance performance. Additionally, the chilled coolant reservoir can serve as a thermal buffer zone to limit heat transfer from the surrounding environment to the coolant contained in the mixing reservoir.

In some embodiments, a chilled coolant is mixed with warm coolant held in a mixing reservoir. The warm coolant can be warmer than the chilled coolant and colder than the subject's skin. The chilled coolant can mix with the warm coolant to reduce the temperature of the coolant in the mixing reservoir. In other embodiments, a stream of chilled coolant is combined with a stream of circulating coolant within a conduit. The streams can mix to produce a stream of cooled coolant.

In yet further embodiments, a circulation circuit can define a primary loop, a chiller apparatus can define a first secondary loop, and a heater apparatus can define a second secondary loop. Chilled coolant and heated fluid can flow independently through the first and second secondary loops. Coolant flowing along the primary loop can cool a liquid-cooled applicator in thermal communication with a subject. In some embodiments, the first loop can be a cooling circuit of a chiller apparatus and can include one or more conduits, pumps, and chilled reservoir. The second loop can be a heating circuit of a heater apparatus and can include one or more conduits, pumps, and chilled reservoir. In some embodiments, the chiller apparatus includes one or more chiller fluidic circuits. Each chiller fluidic circuit can include one or more cooling devices and chilled reservoirs. In one embodiment, the chiller fluidic circuit has a single chilled fluid reservoir and a single cooling device.

In yet other embodiments, a treatment system for cooling subcutaneous lipid-rich cells of a subject comprises a control unit, an applicator, and a thermally insulated supply conduit. The control unit includes at least one coolant reservoir. The applicator is configured to be in thermal communication with the subject's skin to remove thermal energy from the subject. The applicator includes a heat exchanger element through which coolant from the control unit travels such that a substantial portion of thermal energy transferred to the applicator is absorbed by the coolant. The thermally insulated supply conduit fluidically couples the control unit to the applicator. In one embodiment, the thermally insulated supply conduit receives the coolant at a temperature at or below −5° C. from the control unit and delivers the coolant at a temperature at or below 0° C. to the applicator. Other temperature ranges can be achieved.

In some embodiments, a treatment system for cooling subcutaneous lipid-rich cells in a human subject includes an applicator circulation circuit, a chiller apparatus, a cooling device, and a fluidic control system. The applicator circulation circuit can include a pump that drives coolant through the applicator circulation circuit and at least one heat exchanging element configured to transfer heat from the subject's skin to coolant in the heat exchanging element. The chiller apparatus has a chilled fluid reservoir configured to maintain coolant at temperatures lower than a temperature of the coolant in the applicator circulation circuit. In some embodiments, the treatment system includes a cooling device configured to extract heat from the coolant in the chilled reservoir. A fluidic control system can control the cooling/heating of the subject's tissue by varying the rate at which coolant from the chilled reservoir is introduced and mixed into the applicator circulation circuit. The fluidic control system, in some embodiments, includes one or more pumps, valves, conduits, or other fluidic components. Additionally, a return path (e.g., a path defined by a conduit or a spillway) allows excess coolant in the applicator circulation circuit to return to the chilled reservoir.

The treatment system, in some embodiments, can include at least two applicators that share the same applicator circulation circuit with coolant flowing through the applicators in series. In other embodiments, the applicators can share portions of the same applicator circulation circuit with coolant flowing through the applicators in parallel. In one embodiment, a plurality of applicator circulation circuits share a single chilled reservoir and a single cooling device. Each applicator circulation circuit can provide coolant at different temperatures to applicators. As such, the applicators can be thermally decoupled from one another. The chilled reservoir can absorb and release heat to help match the cooling capacity of the cooling device to the cooling demand of one or more applicator circulation circuits. Typically the cooling capacity of the cooling device will exceed the cooling demand of the applicator circulation circuits. The cooling device, in some embodiments, can be cycled off during treatment while the chilled reservoir continues to absorb heat from an applicator circulation circuit, then can be cycled back on periodically as needed to remove the absorbed heat. At other times, the cooling demand of the applicators may exceed the cooling capacity of the cooling device. The chilled reservoir can also allow the cooling burden of the applicator circulation circuits to exceed the thermal capacity of the cooling device, for example, during times of peak cooling demand. The cooling device can remove heat from the chilled reservoir before, during, and/or after the time of peak cooling demand, with the chilled reservoir releasing energy before and/or after the peak demand and absorbing the excess heat burden during peak demand.

The treatment system can further include a heater fluidic circuit which supports controlled warming of the applicator circulation circuit by the controlled introduction of warmed fluid into the applicator circulation circuit. The heater fluidic circuit can contain a warm fluid reservoir containing at least 250 ml of heated coolant which is sufficient to raise the temperature of the coolant in the applicator circulation circuit and to spread the heating load.

At least some treatment systems disclosed herein have control units with multiple states of operation, such as a cooling state, a coasting state, and a heating state. When the control unit is in the cooling state, chilled coolant can be injected into an applicator circulation circuit to ramp down the temperatures of coolant in the applicator circulation circuit. The temperature of coolant in the applicator circulation circuit can fluctuate within a desired temperature range during the cooling state. When the control unit is in the coasting state, the coolant in the applicator circulation circuit may be colder than desired, and the control unit can stop the injection of chilled coolant into the applicator circulation to allow the coolant in the applicator circulation circuit to warm by absorbing heat from the patient and/or surrounding environment. When the control unit is in the heating state, the temperature of a patient applicator of the treatment system can be rapidly increased. For example, the temperature of applicator can be increased at the end of a treatment a session and/or in response to a detected freezing event.

The treatment system can have different modes of operation, including a standby mode, a treatment mode (or treatment cycle), a cooling mode, and a heating mode. In the standby mode, a cooling device can cycle on and off to keep chilled coolant in a chilled reservoir within a standby temperature range. In the treatment mode, the chilled coolant can be used to achieve a desired temperature profile. It is noted that the treatment mode of the treatment system 100 can include multiple modes, such as the cooling mode and the heating mode. Additionally, the control unit can switch between its cooling state, coasting state, and heating state when the treatment system is in the treatment mode to achieve a wide range of different treatment profiles. In the cooling mode, the temperature of the target region can be kept at a low temperature (or within a temperature range). In the heating mode, the temperature of the target region can be kept at a relatively high temperature (or within a temperature range).

In some embodiments, a treatment system for cooling a subcutaneous target region of a human subject comprises an applicator configured to be in thermal communication with the subject's skin and a control unit including a chilled coolant reservoir, a cooling device in thermal communication with the chilled coolant reservoir, and a controller. The cooling device, in some embodiments, is configured to be activated to remove absorbed heat from the coolant held in the chilled coolant reservoir of the treatment system to maintain the coolant at a temperature below a temperature of the coolant in the applicator circulation circuit. The treatment system has a standby mode for pre-cooling the coolant in the chilled reservoir such that the chilled reservoir is capable of absorbing and temporarily storing at least some excess heat in the treatment system when a heat extraction rate for reducing the temperature of the applicator circulation circuit exceeds a heat extraction rate capacity of the cooling device. In some embodiments and during some procedures, the cooling device can be cycled off and on to maintain the temperature of the chilled coolant within a desired temperature range.

In yet other embodiments, a treatment system for cooling subcutaneous lipid-rich cells includes an applicator configured to be in thermal communication with the subject's skin and a control unit. The control unit can include a chiller apparatus that removes heat from an applicator circulation circuit by accepting warmer fluid from the applicator circulation circuit into the chilled reservoir and delivering colder coolant from the chilled reservoir into the applicator circulation circuit. A cooling device of the control unit can continuously or periodically remove heat from coolant contained in the chilled reservoir.

In some embodiments, a treatment system for cooling a subcutaneous target region of a human subject comprises an applicator configured to be in thermal communication with a subject's skin and a control unit. The control unit includes a chilled coolant reservoir, a cooling device in thermal communication with the chilled coolant reservoir, and a controller. The controller contains instructions that, when executed, cause the control unit to reduce a temperature of coolant in the chilled coolant reservoir to a chilled standby temperature using the cooling device, deliver coolant from the chilled coolant reservoir to a circulation circuit to reduce a temperature of the coolant in the applicator circuit, and deliver the cooled coolant in the applicator circulation circuit to the applicator to remove heat from a subcutaneous target region of the subject. In some embodiments, the controller contains instructions that, when executed, cause the cooling device to cycle on and off.

References throughout this specification to "one example," "an example," "one embodiment" or "an embodiment" mean that a particular feature, structure, or characteristic described in connection with the example is included in at least one example of the present technology. Thus, the occurrences of the phrases "in one example," "in an example," "one embodiment" or "an embodiment" in various places throughout this specification are not necessarily all referring to the same example. Furthermore, the particular features, structures, routines, steps or characteristics may be combined in any suitable manner in one or more examples of the technology. The headings provided herein are for convenience only and are not intended to limit or interpret the scope or meaning of the claimed technology.

2. Representative Treatment Systems, Components, and Methods

FIG. 1 shows a treatment system 100 treating a human subject 158 in accordance with one embodiment. The treatment system 100 can include a fluid mixing system 110 and a fluid-cooled applicator 410 ("applicator 410"). The fluid mixing system 110 can include a fluid control unit 130 ("control unit 130") and a circulation circuit 150 which couples the control unit 130 to the applicator 410. A supply conduit 412*a* can carry coolant to the applicator 410, and a return conduit 412*b* can carry the coolant back to the control unit 130. An operator can use a controller 164 to operate the control unit 130. To cool target tissue, heat can be transferred from the subject 158 to the coolant (e.g., coolant at a temperature lower than 37° C.) circulating within the applicator 410. The coolant, carrying the absorbed heat, can be delivered back to the control unit 130. The control unit 130 can remove the absorbed heat and the coolant is delivered back to the applicator 410. To heat target tissue, heat can be transferred from heated coolant, which circulates within the applicator 410, to the subject 158. The coolant can be delivered back to the control unit 130, which reheats the coolant for delivery to the applicator 410.

The control unit 130 can include a chiller apparatus in the form of a chiller fluidic circuit 132 for providing a pre-chilled coolant and a heater apparatus in the form of a heater fluidic circuit 134 for providing heated coolant. The treatment system 100 can spread peak cooling demand over a period of time by using the pre-chilled coolant to absorb and store heat. Additionally, power consumption can be spread over a relatively long period of time. For example, a peak cooling demand associated with reducing the temperature of the applicator circulation circuit at a rapid rate (e.g., by over 15° C. in under 2 minutes) can be met by absorbing as much as half or more of the extracted heat into the thermal mass of a chilled reservoir, then using a cooling device running at relatively low power extracting heat at a relatively slow rate over a much longer period (e.g., 20 minutes) to recover the chilled reservoir to its starting temperature and/or energy condition.

The control unit 130 can have, without limitation, a cooling state, a coasting state, and a heating state to achieve desired thermal performance in any mode of operation of the treatment system 100. The treatment system 100 can change between different modes to produce a wide range of different treatment temperature profiles. In some embodiments, the treatment system 100 has a standby mode, a treatment mode, a cooling mode, and a heating mode. These system modes are discussed separately below.

In the standby mode, the treatment system 100 is ready for use. The chiller fluidic circuit 132 has a cooling device that cycles on and off to keep the chilled coolant at a standby temperature (or within a standby temperature range).

In the system cooling mode (which can be part of the treatment mode of the treatment system 100), the control unit 130 may operate predominantly in a cooling state. When the control unit 130 is in the cooling state, the pre-chilled coolant can be used to reduce the temperature of coolant that flows along a flow path 133 (shown in dashed line in FIG. 1). At times in the cooling mode, however, the control unit 130 may operate in a coasting state with coolant flowing continuously along the flow path 133 without mixing chilled or heated coolant such that coolant in the applicator circulation circuit gradually warms as the coolant continues to extract heat from the target tissue. At still other times in cooling mode of the treatment system 100, the control unit 130 may operate in a heating state, for example to correct a cooling mode control overshoot. When the control unit 130 is in the heating state, heated coolant can be used to warm the coolant that flows along the flow path 133.

In the system heating mode (which can be part of the treatment mode of the treatment system 100), the control unit 130 may operate predominately in a heating state, providing heated coolant to keep target tissue at a relatively high temperature. Even if the heater coolant is heated only by ambient air, the heated coolant may be warmer than the subject's skin so as to support a tissue heating operating mode (e.g., the heating mode of the treatment system 100 may take place after the target tissue has been cooled to well below ambient temperature by the device).

Figure 2:
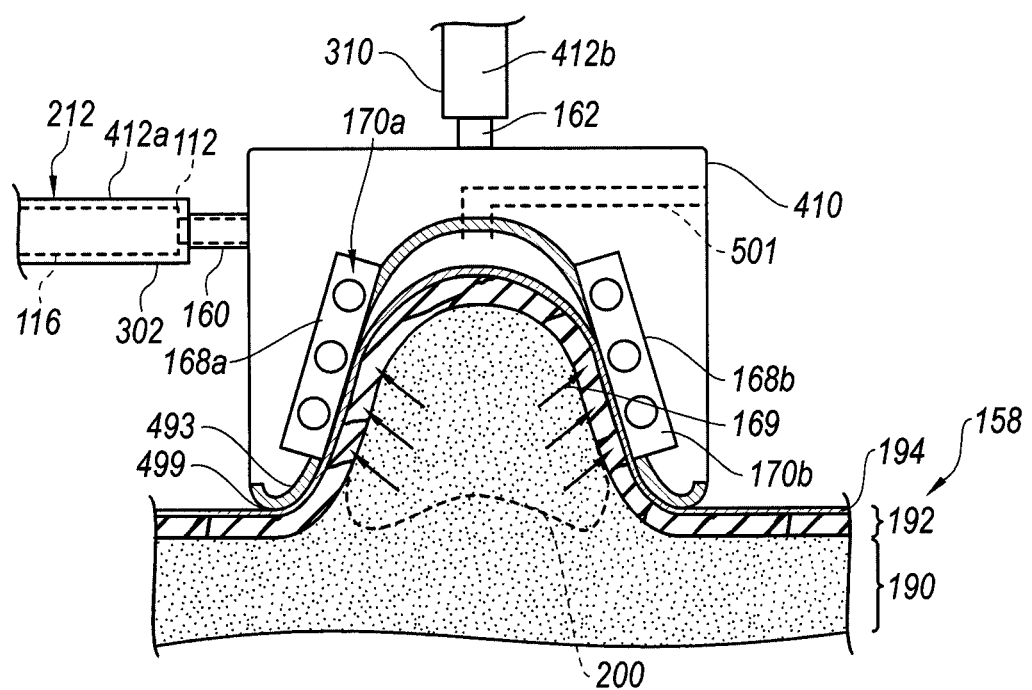
FIG. 2 is a cross-sectional view of an applicator positioned on a subject in accordance with one embodiment.

FIGS. 1 and 2 show the applicator 410 in thermal communication with the subject's skin. FIG. 2 is a cross-sectional view of the applicator 410 cooling a subcutaneous target region 200. The applicator 410 can include an inlet 160 for receiving coolant from the supply conduit 412a and an outlet 162 for delivering coolant to the return conduit 412b. The coolant can flow through channels 170a, 170b (collectively, "channels 170") in heat exchanger elements 168a, 168b, respectively. To cool tissue, heat (represented by arrows with one arrow labeled 169) can be transferred from subcutaneous, lipid-rich tissue 190 to the chilled coolant in the channels 170. To heat tissue, heat can travel in the opposite direction.

Without being bound by theory, the selective effect of cooling is believed to result in, for example, membrane disruption, cell shrinkage, disabling, damaging, destroying, removing, killing or other methods of lipid-rich cell alteration. Such alteration is believed to stem from one or more mechanisms acting alone or in combination. It is thought that such mechanism(s) trigger an apoptotic cascade, which is believed to be the dominant form of lipid-rich cell death by non-invasive cooling. In any of these embodiments, the effect of tissue cooling is to selectively reduce lipid-rich cells by an desired mechanism of action, such apoptosis, lipolysis, or the like.

Apoptosis, also referred to as "programmed cell death", is a genetically-induced death mechanism by which cells self-destruct without incurring damage to surrounding tissues. An ordered series of biochemical events induce cells to morphologically change. These changes include cellular blebbing, loss of cell membrane asymmetry and attachment, cell shrinkage, chromatin condensation and chromosomal DNA fragmentation. Injury via an external stimulus, such as cold exposure, is one mechanism that can induce cellular apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" Cryobiology 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by macrophages. As a result, phagocytes can engulf and remove the dying cells (e.g., the lipid-rich cells) without eliciting an immune response. Temperatures that elicit these apoptotic events in lipid-rich cells may contribute to long-lasting and/or permanent reduction and reshaping of subcutaneous adipose tissue.

One mechanism of apoptotic lipid-rich cell death by cooling is believed to involve localized crystallization of lipids within the adipocytes at temperatures that do not induce crystallization in non-lipid-rich cells. The crystallized lipids selectively may injure these cells, inducing apoptosis (and may also induce necrotic death if the crystallized lipids damage or rupture the bi-lipid membrane of the adipocyte). Another mechanism of injury involves the lipid phase transition of those lipids within the cell's bi-lipid membrane, which results in membrane disruption or dysfunction, thereby inducing apoptosis. This mechanism is well-documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" Heart Failure Reviews, 8, 277-284 (2003). Other possible mechanisms of adipocyte damage, described in U.S. Pat. No. 8,192,474, relates to ischemia/reperfusion injury that may occur under certain conditions when such cells are cooled as described herein. For instance, during treatment by cooling as described herein, the targeted adipose tissue may experience a restriction in blood supply and thus be starved of oxygen due to isolation while pulled into, e.g., a vacuum cup, or simply as a result of the cooling which may affect vasoconstriction in the cooled tissue. In addition to the ischemic damage caused by oxygen starvation and the buildup of metabolic waste products in the tissue during the period of restricted blood flow, restoration of blood flow after cooling treatment may additionally produce reperfusion injury to the adipocytes due to inflammation and oxidative damage that is known to occur when oxygenated blood is restored to tissue that has undergone a period of ischemia. This type of injury may be accelerated by exposing the adipocytes to an energy source (via, e.g., thermal, electrical, chemical, mechanical, acoustic or other means) or otherwise increasing the blood flow rate in connection with or after cooling treatment as described herein. Increasing vasoconstriction in such adipose tissue by, e.g., various mechanical means (e.g., application of pressure or massage), chemical means or certain cooling conditions, as well as the local introduction of oxygen radical-forming compounds to stimulate inflammation and/or leukocyte activity in adipose tissue may also contribute to accelerating injury to such cells. Other yet-to-be understood mechanisms of injury may exist.

In addition to the apoptotic mechanisms involved in lipid-rich cell death, local cold exposure is also believed to induce lipolysis (i.e., fat metabolism) of lipid-rich cells and has been shown to enhance existing lipolysis which serves to further increase the reduction in subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" Aviation, Space and Environmental Medicine 70, 42-50 (1999).

One expected advantage of the foregoing techniques is that the subcutaneous lipid-rich cells in the target region 200 can be reduced generally without collateral damage to non-lipid-rich cells in the same region. In general, lipid-rich cells can be affected at low temperatures that do not affect non-lipid-rich cells. As a result, lipid-rich cells, such as those associated with cellulite, can be affected while other cells in the same region are generally not damaged even though the non-lipid-rich cells at the surface (e.g., cells in the dermis 192 and/or epidermis 194) may be subjected to even lower temperatures than those to which the lipid-rich cells are exposed.

Applying the applicator 410 with pressure and/or a vacuum can enhance treatment. In general, the subject 158 can have a body temperature of about 37° C., and blood circulation is one mechanism for maintaining a constant body temperature. As a result, blood flow through the subcutaneous layer 190 can be viewed as a heat source that counteracts the cooling of the subdermal fat. As such, cooling the tissue of interest requires not only removing the heat from such tissue but also that of the blood circulating through this tissue. Thus, temporarily reducing or eliminating blood flow through the target region 200 (e.g., applying the applicator 410 with pressure) can improve the efficiency of tissue cooling and avoid excessive heat loss through the dermis 192 and epidermis 194. Additionally, a vacuum can pull skin away from the body which can assist in cooling targeted underlying tissue.

The heat exchanger elements 168a, 168b (collectively "heat exchanger elements 168") can be formed from a variety of thermally conductive materials, including but not limited to, copper, aluminum, or other materials, preferably materials with a relatively high thermal conductivity. In some embodiments, materials with moderate or low thermal conductivities such as plastics can be used to form useful heat exchanger elements 168. The thermally conductive materials can transfer heat from the subject 158 to the coolant in the channels 170. When the applicator 410 is maintained below the ambient temperature, the coolant can carry away substantially all of the extracted heat.

FIG. 2 shows a vacuum port 501 for drawing a vacuum and the subject's tissue located in a cavity 499 defined by a vacuum cup 493. In some embodiments, a conduit for drawing the vacuum is bundled together with one or both conduits 412a, 412b. In other embodiments, a standalone vacuum conduit can couple the vacuum port 501 to a vacuum device of the control unit 130 (FIG. 1). The treatment system 100 can also include a belt applicator (either of which may be used in combination with a massage or vibrating capability).

The applicator 410 may be designed to treat identified portions of the patient's body, such as chin, cheeks, arms, pectoral areas, thighs, calves, buttocks, abdomen, "love handles", back, and so forth. For example, a vacuum applicator may be applied at the back region, and a belt applicator can be applied around the thigh region, either with or without massage or vibration. The control unit 130 can output coolant independently to each applicator. Exemplary applicators and their configurations usable or adaptable for use with the treatment system 100 are described in, e.g., commonly assigned U.S. Pat. No. 7,854,754, U.S. application Ser. No. 13/013,579, and U.S. Patent Publication Nos. 2008/0077201, 2008/0077211; and 2008/0287839. U.S. Pat. No. 7,854,754, U.S. application Ser. No. 13/013,579, and U.S. Patent Publication Nos. 2008/0077201, 2008/0077211; and 2008/0287839 are incorporated by reference in their entireties. In further embodiments, the treatment system 100 may also include a patient protection device (not shown) incorporated into or configured for use with the applicator 410. The patient protection device can prevent the applicator from directly contacting a patient's skin to reduce the likelihood of cross-contamination between patients, minimize cleaning requirements for the applicator, and limit or minimize damage to non-targeted tissue. The patient protection device may also include or incorporate various storage, sensing, computing, and communications devices, such as a radio frequency identification (RFID) component, allowing for example, used to be monitored and/or metered. Exemplary patient protection devices are described in commonly assigned U.S. Patent Publication No. 2008/0077201, which is incorporated by reference in its entirety.

Because the applicator 410 can be cooled with a low-temperature coolant (e.g., coolant at a temperature at or below about 0° C.), the supply conduit 412a can be configured to limit or inhibit condensation, which can lead to, for example, cold water dripping onto the subject 158, bed, or floor of a treatment room. When the cooled coolant flows through the conduit 412a, substantially no condensation forms on an exterior surface 212 (FIG. 2), even over relatively long periods of time (e.g., 30 minutes to 2 hours). The supply conduit 412a is a multi-layered extruded tube that comprises, for example, an outer thermally insulating layer (e.g., a foam layer comprising open-cell foam, closed-cell foam, combinations thereof, etc.) and an inner layer suitable for contacting coolants. The supply conduit 412a can receive coolant at a temperature equal to or below about −10° C. and deliver the coolant at a temperature less than about 0° C. As used herein, the term "conduit" is a broad term that can include, without limitation, one or more tubes, hoses, or other components through which fluid is capable of flowing. In some embodiments, the supply conduit 412a can include multiple tubes coupled together by, for example, valves (e.g., check valves, one-way valves, etc.) or other fluid components.

Figure 3:
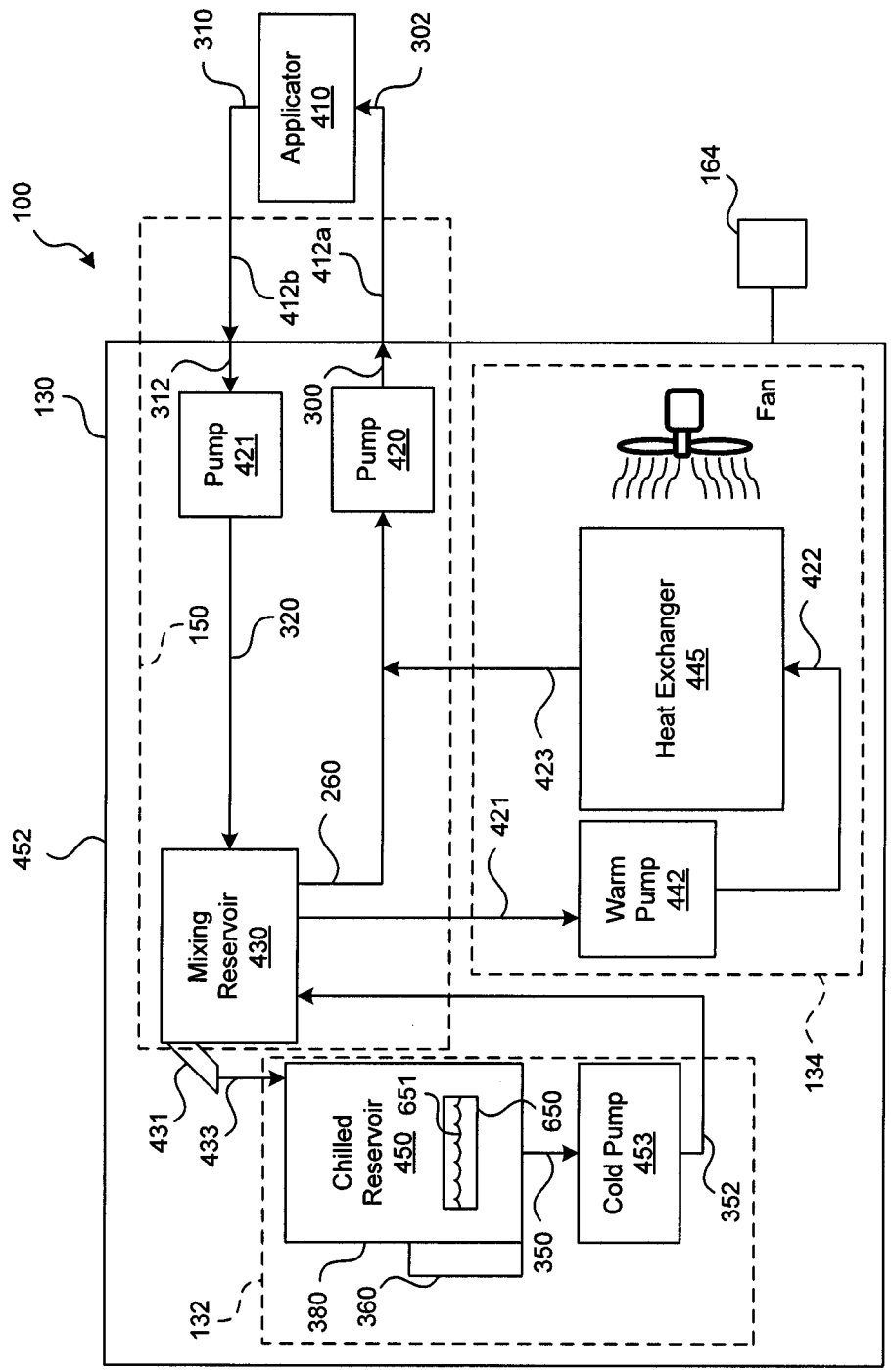
FIG. 3 is a schematic illustration of a treatment system in accordance with an embodiment of the disclosure.

FIG. 3 is a schematic illustration of the treatment system 100 in accordance with an embodiment of the disclosure. The applicator circulation circuit 150 can include a mixing reservoir 430 and one or more drive devices in the form of pumps 420, 421. The mixing reservoir 430 can be a vessel for holding a desired volume of coolant. In some embodiments, the reservoir 430 includes, without limitation, one or more containers, tanks, or other suitable containers with a fluid holding capacity of at least about 400 milliliters, or more preferably between about 100 and 400 milliliters, or more preferably 30 milliliters or less. Smaller mixing reservoirs are preferred so as to reduce the heat extraction required to ramp down the temperature of the thermal mass contained in circulation circuit 150. However, the mixing reservoir 430 can have other holding capacities selected based on, for example, the dimensions of features located in the mixing reservoir. To enhance heat transfer, the coolant mixing fins or an active mixing device (e.g., a stir rod, a propeller, or like) can be used to further mix coolant held in the mixing reservoir 430. The thermal mass of the coolant in the mixing reservoir 430 (i.e., when the mixing reservoir 430 is completely filled with coolant) the can be equal to or less than about 70%, 50%, or 30% of the total thermal mass of the applicator circulation circuit 150. In some embodiments, the thermal mass of the coolant in the mixing reservoir 430 can be less than about 10% of the total thermal mass of applicator circulation circuit 150.

A housing 452 may reduce the absorption of heat from the ambient air to reduce or limit the electrical power draw for cooling the coolant. A conduit 260 can fluidically couple the mixing reservoir 430 to the pump 420. The pump 420 can drive the coolant through the supply conduit 412a and can include, without limitation, one or more positive displacement pumps (e.g., reciprocating pumps, gear pumps, rotary vane pumps, etc.), rotodynamic pumps, or other types of drive devices capable of pressurizing fluids (e.g., liquid coolants). The number, types, and configurations of the pumps can be selected based on, for example, the desired working pressures.

The conduit 412a has an upstream end 300 coupled to the pump 420 and a downstream supply end 302 coupled to the applicator 410. The upstream end 300 receives fluid from the pump 420, and the downstream end 302 delivers the fluid to the applicator 410. The return conduit 412b has an upstream return end 310 coupled to the applicator 410 and a downstream end 312 coupled to the pump 421. A conduit 320 fluidically couples the pump 421 to the reservoir 430.

FIG. 3 shows a chiller apparatus in the form of a chiller fluidic circuit 132 that can include a chilled reservoir 450, a cold pump 453 ("pump 453"), and conduits 350, 352. The chilled reservoir 450 can hold coolant (referred to as "chilled coolant") at a relatively low temperature and the chiller fluidic circuit 132 can include, without limitation, a refrigeration unit, a cooling tower, a thermoelectric chiller, a cartridge of phase change material, or any other device capable of removing heat from coolant. In some embodiments, the chilled reservoir 450 can have a fluid holding capacity of at least about 8 liters, or to reduce the overall volume and weight of system 100, preferably between about 5 and 8 liters, or more preferably between about 2 and 5 liters. However, the chilled reservoir 450 can have other holding capacities selected based on, for example, the frequency and duration of peak thermal loads, the amount of heat that the chilled reservoir 450 absorbs during peak thermal loads, the specific heat capacity of the fluid used, and the allowable temperature span between the temperature of the fluid in the chilled reservoir 450 in the pre-cooled condition and at the end of the peak thermal loading. The amount of heat that the chilled reservoir 450 must absorb during peak thermal loads is determined by a number of factors including, for example, the rate of temperature reduction and the duration of the temperature ramp down phase, the holding capacity and associated thermal mass of the applicator circulation circuit 150 which includes mixing reservoir 430, the rate of heat removal from the tissue, the magnitude of parasitic heat loads from ambient, and the degree to which the peak thermal loads exceed the cooling capacity of the heat removal mechanism, such as the cooling device 360 in FIG. 3, used to extract heat from the chilled reservoir 450.

In operation, the chilled reservoir 450 can hold pre-chilled coolant (i.e., cold coolant) at a standby temperature lower than the desired treatment temperature for altering tissue. For example, the standby temperature can be in a standby temperature range of about −30° C. to about 0° C. The pre-chilled coolant can be selectively mixed with warmer coolant in the mixing reservoir 430 to reduce the average temperature of coolant in the mixing reservoir 430. As indicated by arrows in FIG. 3, the coolant from the mixing reservoir 430 flows through the conduit 260 and into the pump 420. The pump 420 can pressurize and drive the coolant through the supply conduit 412a, the applicator 410, and the return conduit 412b. In some embodiments, the pump 421 can draw the coolant through the applicator 410 and conduit 412b. As such, the coolant in the applicator 410 can be at relative low pressures, including sub-atmospheric pressures.

The applicator circulation circuit 150 can include any number of pumps positioned at various locations and, in some embodiments, includes a single pump. For example, the pump 421 of FIG. 3 can be removed. In other embodiments, the applicator circulation circuit 150 can include the pump 421 and the pump 420 can be removed. Additionally, heaters can be positioned at different locations along the fluid circuit 150. Such heaters can include, without limitation, one or more electric heaters capable of converting electrical energy to thermal energy. For example, an in-line heater can be positioned along the conduit 260. Additionally, valves can be located at various locations along the flow path 133 (FIG. 1). By way of example, one-way valves can be positioned along one or more of the conduits 260, 412a, 412b, 320, 352 to inhibit or prevent backflow. Additionally or alternatively, one-way valves can be positioned within the mixing reservoir 430, pumps 420, 421, and/or the applicator 410.

FIG. 3 shows a cooling device 360 configured to reduce the temperature of coolant held in the chilled reservoir 450. In one embodiment, the cooling device 360 can include, without limitation, one or more compressors, condensers, heat exchanger elements, and/or valves (e.g., throttling valves, expansion valves, etc.) that cooperate to cool the coolant based on, for example, the vapor-compression refrigeration cycle or other refrigeration cycle. In other embodiments, the cooling device 360 includes thermoelectric elements, such as Peltier devices. In some embodiments, the cooling device 360 includes both a refrigeration unit and a thermoelectric element.

If coolant leaks from the applicator circulation circuit 150, coolant from the chilled reservoir 450 can be delivered to the mixing reservoir 430, thus replenishing the coolant in the applicator circulation circuit 150. Once coolant in the mixing reservoir 430 reaches a target level, excess coolant can be delivered back to the chilled reservoir 450 via a passive leveling element in the form of a spillway 431. In one embodiment, the spillway 431 includes an angled ramp that allows excess coolant to flow down the ramp and into the chilled reservoir 450. FIG. 3 shows coolant (represented by arrow 433) falling from the spillway 431 and through an open upper end 380 of the chilled reservoir 450. Advantageously, the spillway 431 is capable of limiting the fluid level of coolant in the mixing reservoir 430 without utilizing complicated valves, fluid level sensors, active fluid leveling devices (e.g., pumps), or other components susceptible to malfunction and failure. In other embodiments, the spillway 431 includes one or more conduits extending from a sidewall of the mixing reservoir 430 to the chilled reservoir 450. Such conduits can include one or more valves for managing fluid flow between the mixing reservoir 430 and the chilled reservoir 450, for example, a one-way check valve in the conduit could open when the pump 352 drives coolant into the applicator circulation circuit 150 and raises the pressure in the applicator circulation circuit 150 (including the mixing reservoir 430).

The heater fluidic circuit 134 can include a driver in the form of a warm pump 442 ("pump 442"), a heat exchanger 445, and conduits 420, 422, and 423. The pump 442 can draw coolant from the conduit 260, pressurize the coolant, and deliver the pressurized coolant to the conduit 422. When the coolant in circulation circuit 150 is colder than desired, the heat exchanger 445 can heat the coolant. In air-heated embodiments, the heat exchanger 445 can include, without limitation, one or more drive devices (e.g., fans, pumps, etc.) that can force air across thermal elements, such as finned tubes, which transfer thermal energy to the coolant. The forced air can be warm air, room temperature air, or the like. Other types of heat exchangers (e.g., liquid-to-liquid heat exchangers) can be used.

When the treatment system 100 is in the standby mode, the cooling unit 130 can be ready to rapidly cool target tissue. The chilled coolant in the chilled reservoir 450 can be maintained at a temperature equal to or less than about −15° C. while coolant in the mixing reservoir 430 may be at a temperature near room temperature. In some embodiments, the chilled coolant in chilled reservoir 450 can be maintained at a temperature in a range of about −22° C. to about −18° C. The treatment system 100 can switch to a treatment mode and begin a treatment cycle. The cooling unit 130 can reduce the temperature of the coolant in the mixing reservoir 430 and start reducing the temperature of the target region (e.g., target region 200 of FIG. 2). The rate of heat transfer from the subject to the circulating coolant can be the greatest during the ramp down portion of a treatment cycle because the tissue in close proximity to heat exchanging elements 168 is rapidly cooled from near normal body temperature to a treatment dwell temperature. In some embodiments, the control unit 130 delivers coolant at about −15° C. to about 45° C. to the applicator 410 during a ramp portion of a treatment mode, and delivers coolant at about −15° C. to about −5° C. to the applicator during a dwell portion of the treatment cycle. Other temperature ranges can be used.

In the ramp down portion of a treatment cycle, the temperature of the coolant in circulation circuit 150 and the tissue in close proximity to heat exchanging elements 168 can be rapidly reduced to a temperature less than about 0° C. in about 3 minutes to about 6 minutes. The length of the ramp time period can be selected based on the procedure to be performed, but a short ramp down period is desirable for minimizing overall procedure time. In addition to high heat loads from the tissue during rapid ramp down, the reduction in temperature of the thermal mass of circulation circuit 150 releases large quantities of heat contributing to very high peak heat loads. In many cases, the cooling device 360 may not be able to keep up with the peak heat loads resulting in the temperature of the coolant in the chilled reservoir 450 increasing by, for example, about 1° C. to about 15° C. For example, in some cases the temperature of the chilled coolant in the chilled reservoir 450 can start at about −20° C. at the beginning of the ramp down and may rise to about −15° C. by the end of the ramp mode. At the end of the ramp down, the thermal loads generally reduce to levels below the heat removal rate capacity of cooling device 360 allowing cooling device 360 to keep up with treatment heat loads and apply excess cooling capacity to drive the temperature of chilled reservoir 450 back down in preparation for the next peak heating load. In some embodiments, the ramp down portion of the treatment cycle and the corresponding peak heat load from the applicator circulation circuit can last about 1 minute to about 5 minutes, but the chilled reservoir 450 can spread the peak cooling load required of cooling device 360 over a longer period of time (e.g., about 5 minutes to about 20 minutes).

During the dwell portion of a treatment cycle, heat can be removed from circulation circuit 150 to keep the applicator 410 within a desired temperature range as heat continues to be extracted from target region 200. Heat removed from circulation circuit 150 passes through the chilled reservoir 450. The cooling device 360 can extract heat from chilled reservoir 450, including heat absorbed during a dwell segment of a treatment cycle and heat absorbed from the applicator circulation circuit earlier in the treatment cycle during a ramp down segment. After the chilled coolant is at a desired temperature, the cooling device 360 can be cycled off allowing chilled reservoir 450 to continue to absorb heat removed from circulation circuit 150. The cooling device 360 can be cycled back on periodically as needed to lower the temperature of the chilled coolant in chilled reservoir 450. The cooling device 360, in some embodiments, keeps the chilled coolant in a temperature range of −25° C. to about −15° C., or between −22° C. to about −18° C. by cycling on and off. In some embodiments, the cooling device 360 has one or more variable speed device(s) (e.g., a variable speed refrigerant compressor, a variable speed condenser fan, etc.) that cooperate to provide a reduced rate of heat removal from coolant in the chilled reservoir 450 which can reduce the need to cycle the cooling device on and off when cooling demands are low (e.g., during a dwell segment of a treatment cycle).

When the temperature of the coolant in the mixing reservoir 430 is higher than desired, the chiller fluidic circuit 132 can deliver chilled coolant from the chilled reservoir 450 to the mixing reservoir 430. The chilled coolant can lower the overall temperature of the coolant in the mixing reservoir 430. As the chilled coolant is pumped into the mixing reservoir 430, the fluid level of the coolant can rise until it reaches the spillway 431. The excess coolant can flow through the spillway 431 and back into the chilled reservoir 450, thereby causing a temperature increase of coolant in the chilled reservoir 450. The cooling device 360 can cool the coolant in the chilled reservoir 450 to prevent or limit such temperature increase.

When the temperature of coolant in the mixing reservoir 430 is slightly colder than the target temperature, the pump 453 can be slowed or stopped to allow heat absorbed by the applicator 410 to slowly raise the temperature of the circulating coolant, thereby raising the temperature of coolant in the mixing reservoir 430. When the coolant in the mixing reservoir 430 is much colder than desired (e.g., more than slightly colder than the target temperature), the pump 442 can be activated to draw coolant from the conduit 260. The heat exchanger 445 heats the coolant and delivers it through the conduit 423. The heated coolant can mix (i.e., combine) with the coolant in the conduit 260.

When coolant in the mixing reservoir 430 is significantly colder than the ambient temperature, the heat exchanger 445 can scavenge a significant amount of heat from ambient air (e.g., more thermal energy than the energy required to operate the pump 442). As such, the heat exchanger 445 can efficiently heat the coolant while minimizing energy consumption. Additionally, heating the coolant using ambient air can reduce the power consumption of treatment system 100, and can reduce the total net heat exhausted by treatment system 100 into the treatment room.

The cooling/heating rates of the chiller fluidic circuit 132, heater fluidic circuit 134, and/or the applicator circulation circuit 150 can be decoupled, thereby providing the ability to cool the applicator 410 independently of operation of the cooling device 260. Additionally or alternatively, the chiller fluidic circuit 132 and/or heater fluidic circuit 134 can be cycled on/off independent of the mode of operation of the treatment system 100. For example, the cooling device 360 can cycle on/off while control unit 130 delivers coolant at a constant temperature to the applicator 410. Additionally, the cooling device 260 can be small-capacity refrigerator unit because of the decoupled cooling/heating rates of the chiller fluidic circuit 132, heater fluidic circuit 134, and/or the applicator circulation circuit 150.

Referring to FIG. 3, the heat exchanger 445 can be incorporated into a refrigeration system and used with condenser (e.g., a condenser for a vapor compression refrigeration system) to extract heat from a hot side of a refrigeration system, thereby enhancing refrigeration performance when cold coolant is warmed in the heat exchanger 445. By way of example, a vapor refrigerant from the cooling device 360 can be delivered to the heat exchanger 445, which can condense the refrigerant by transferring heat from the refrigerant to coolant. As a result, the heat exchanger 445 can heat the coolant while enhancing performance of the cooling device 360. The condensed liquid refrigerant can be delivered back to the cooling device 360. When the coolant in the mixing reservoir 430 is warmer than ambient air and cooler than the target temperature, the pumps 453 and 442 can be stopped and the coolant can be warmed by absorbing heat from the subject and/or ambient. When the temperature of coolant in the mixing reservoir 430 is higher than the ambient temperature and significantly higher than the target temperature, the pump 453 can be off. The pump 442 can be activated to drive coolant through the heat exchanger 445, which can deliver heat from the coolant to the surrounding ambient air.

The pumps (e.g., pumps 420, 421, 442, 453) can be variable speed positive displacement pumps, such as gear pumps, capable of achieving a flow rate substantially proportional to pump speeds. Some positive displacement pumps can provide feedback signals to allow measurement of pump shaft speeds and associated flow rate. Monitoring devices, such as sensors, can be at various locations throughout the treatment system 100. For example, sensors can be located within the applicator 410, reservoirs (e.g., mixing reservoir 430, chilled reservoir 450, etc.), heat exchanger 445, or other suitable components. Additionally or alternatively, sensors can be positioned at various locations along the conduits to monitor temperatures or pressure losses and optimize performance. Additionally, one or more valves can be positioned along the conduit 352 to prevent backflow from the mixing reservoir 430 to the chilled reservoir 450. The number and types of pumps, sensors, valves, and other components can be selected to achieve the desired working pressures, flow rates, and temperature profiles. Additionally, the heater fluidic circuit 134 can be removed from the treatment system 100. For example, ambient heat or heat from the subject can cause heating of the coolant. Alternatively, the heater fluidic circuit 134 can be replaced with one or more heaters, for example an inline heater placed in applicator circulation circuit 150.

The controller 164 can exchange data with the applicator 410 via control lines 112, 116 (FIG. 2). Alternatively, the controller 164 can communicate with the applicator 410 via a wireless or an optical communication link. The controller 164 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry. Secure storage may also be implemented as a secure flash memory, secure serial EEPROM, secure field programmable gate array, or secure application-specific integrated circuit. The controller 164 can receive data from an input/output device 171 (shown as a touch screen in FIG. 1), transmit data to an output device, and/or exchange data with a control panel (not shown).

Temperature sensors (e.g., sensors proximate to an interface between the applicator 410 and the patient's skin 194, a patient protection device, etc.) can be used to determine whether a temperature or heat flux is sufficiently close to the target temperature or heat flux. It will be appreciated that while a region of the body (e.g., adipose tissue) has been cooled or heated to the target temperature, in actuality that region of the body may be close but not equal to the target temperature, e.g., because of the body's natural heating and cooling variations. Thus, although the treatment system 100 may attempt to heat or cool the tissue to the target temperature or to provide by a target heat flux, a sensor may measure a sufficiently close temperature. If the target temperature has not been reached, the temperature of the coolant can be raised or lowered to maintain the target temperature or "set-point" to selectively affect lipid-rich subcutaneous adipose tissue. When the prescribed segment duration expires, the controller 164 may apply the temperature and duration indicated in the next treatment profile segment.

Figure 4:
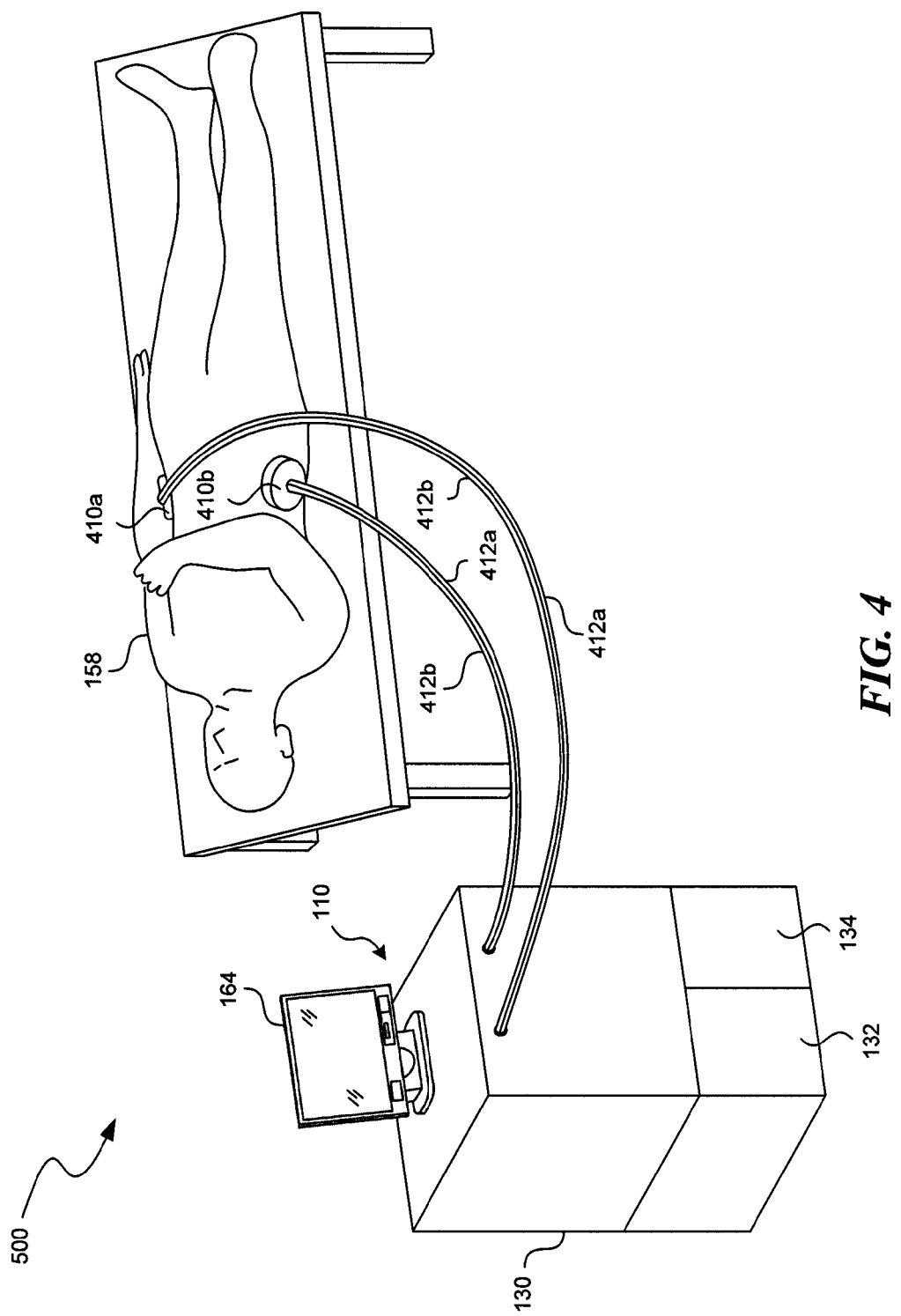
FIG. 4 is a schematic illustration of a treatment system for treating two target regions of a subject in accordance with one embodiment.
Figure 5:
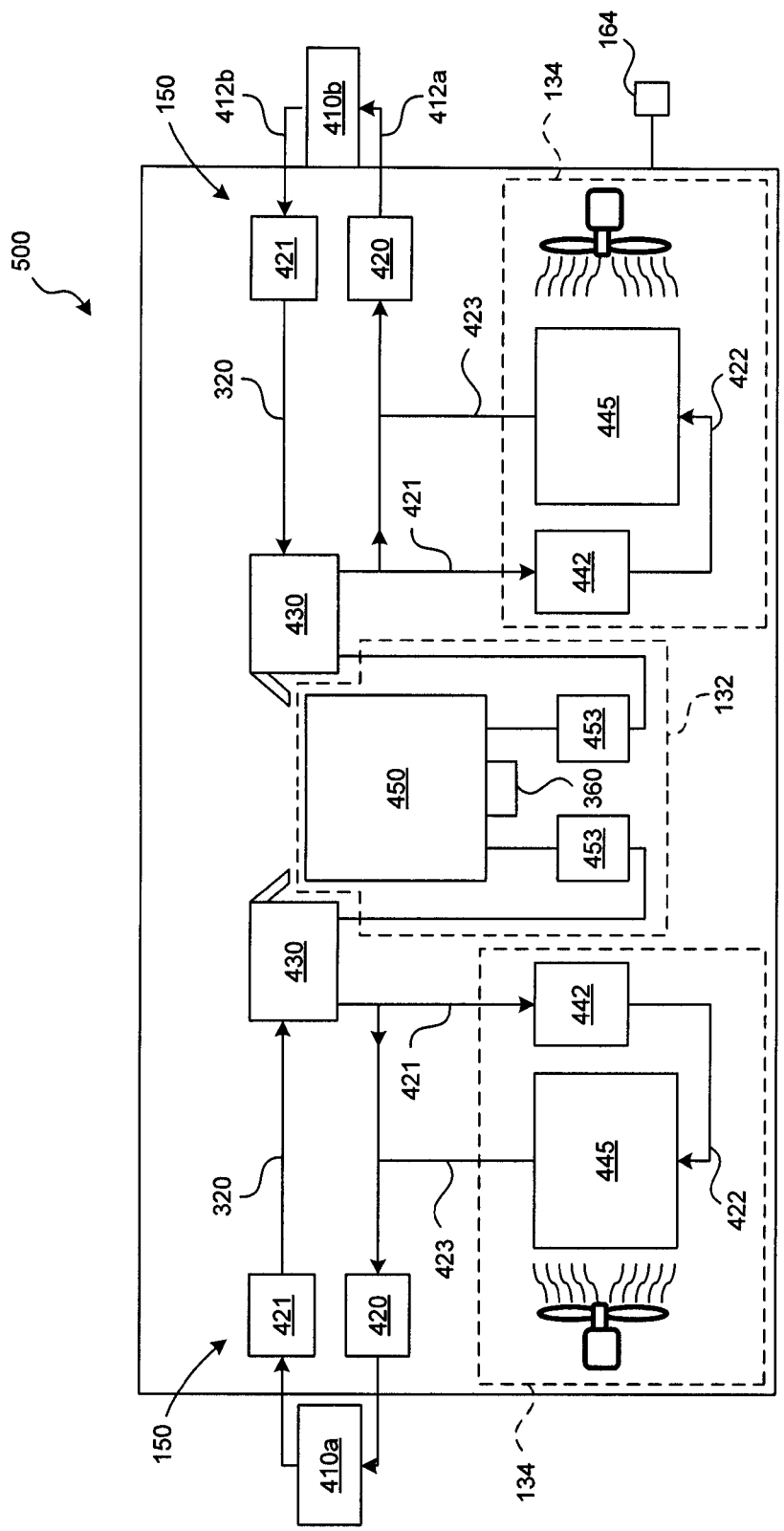
FIG. 5 is a schematic illustration of a treatment system in accordance with one embodiment of the disclosure.

FIGS. 4 and 5 are schematic illustrations of a treatment system 500 that can operate in accordance with the general principles described in reference to FIGS. 1-3. Referring to FIG. 4, the treatment system 500 can include multiple applicators 410 (shown individually as 410*a*, 410*b*) treating the subject 158. The chiller fluidic circuit 132 can be configured to hold a sufficient volume of chilled fluid to concurrently or sequentially cool multiple target regions at desired rates. For example, the chiller fluidic circuit 132 of FIG. 4 can have a fluid holding capacity greater than the fluid holding capacity of the chiller fluidic circuit 132 of FIG. 3. The fluid holding capacity of the chiller fluidic circuit 132 of FIG. 4 can be selected based on, for example, the number of applicators, types of applications, treatment protocol(s), and number of treatment sessions to be performed.

Referring to FIG. 5, the chiller fluidic circuit 132 can include a single chilled reservoir 450 to limit the overall fluid volume held in the temperature system 500. The cooling device 360 can cool the entire volume of chilled coolant in the chilled reservoir 450. Coolant in the mixing reservoirs 430 can be at the same or different temperatures based on operation of pumps 453. In other embodiments, the two mixing reservoirs 430 can receive chilled coolant from two separate chilled fluid reservoirs (not shown), which can be kept at different temperatures.

The controller 164 can have a single treatment session state of operation for delivering coolant to only one of the applicators 410*a*, 410*b* and a multiple treatment session state of operation for delivering coolant to both applicators 410*a*, 410*b*. In some procedures, the controller 164 can alternate between the single and multiple treatment session state of operation. The controller 164 can have other states of operation. In operation, each applicator 410*a*, 410*b* can cool a target region at the same or different rate as the applicator 410 of FIGS. 1-3. Additionally, the chiller fluidic circuit 132 can hold chilled coolant at a lower temperature than the chilled coolant of FIGS. 1 and 3 to compensate for thermal loading associated with multiple applicators 410 that concurrently or sequentially perform love handle treatment protocols, thigh treatment protocols, or the like. The controller 164 can contain instructions that, when executed, cause the controller 164 to command the chiller fluidic circuits 132 to deliver the chilled coolant to the applicator circulation circuits 150 to lower temperature coolant delivered to the applicators 410. The controller 164 can also command the heater fluidic circuit 134 to deliver the heated coolant to the applicator circulation circuits 150 to raise the temperature of the coolant delivered to the applicators 410. Additionally or alternatively, the controller 164 can contain instructions for commanding the heater fluidic circuit 134 to deliver heated coolant into the applicator circulation circuit 150 based, at least in part, on one or more signals from a temperature monitoring device (e.g., one or more temperature sensors).

Figure 6:
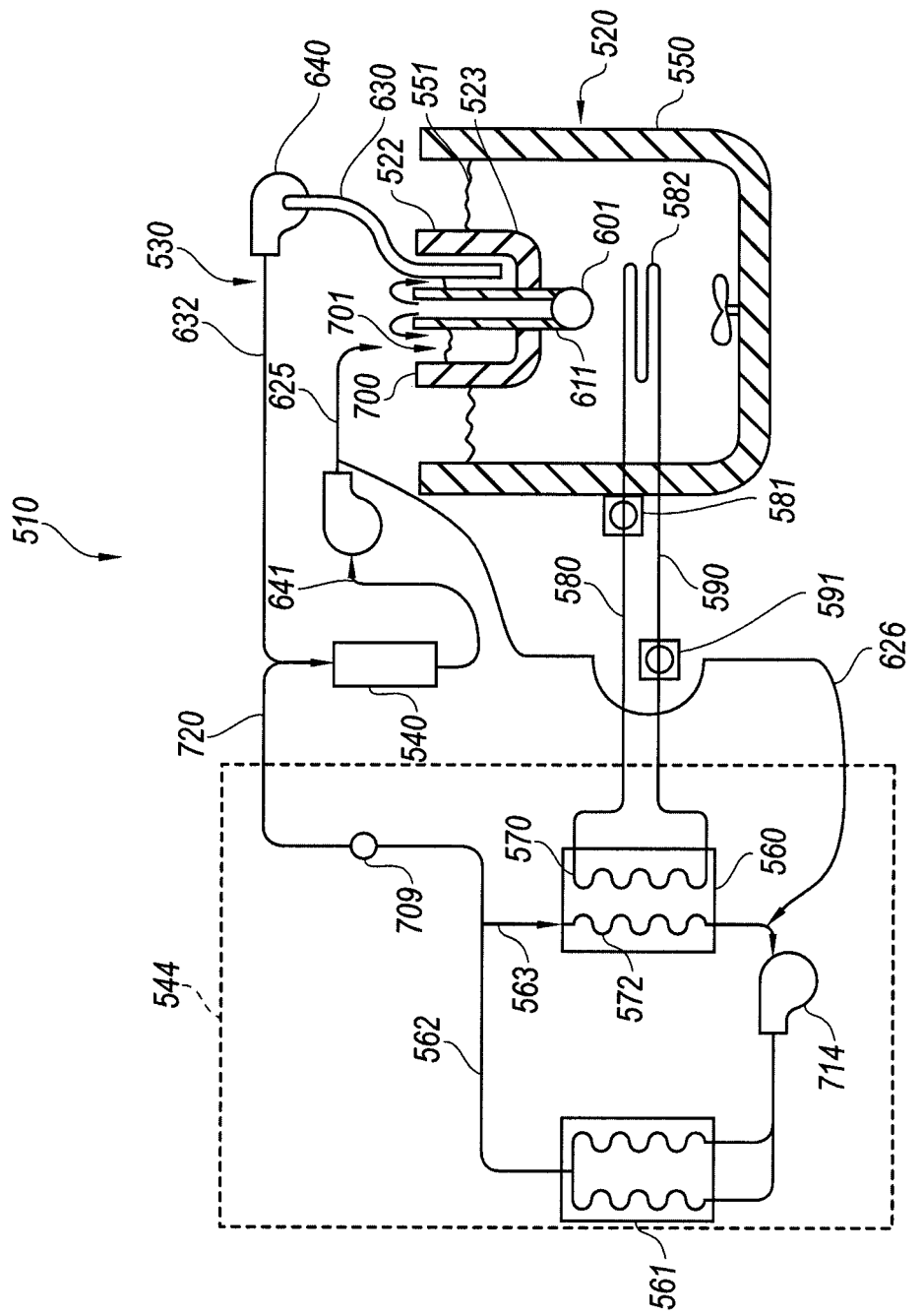
FIG. 6 is a schematic illustration of a treatment system including a cooling system operating on a refrigeration cycle in accordance with one embodiment of the disclosure.

FIG. 6 is a schematic illustration of a treatment system 510 in accordance with one embodiment. The cooling system 544 can operate on a vapor-compression refrigeration cycle and can include a condenser 560 and an evaporator 582. Cooling system 544 can contain refrigerant R-22, refrigerant R134a, refrigerant R404a, refrigerant 410A, or other suitable refrigerants capable of being used in, for example, a single stage vapor-compression system. Compressor 591 located along element 590 can raise the pressure of the refrigerant and raise the temperature of the refrigerant flowing through element 590. The refrigerant enters the condenser 560 at a temperature in a range of about 10° C. to about 40° C. above ambient temperature and flows through a channel 570. Heat is extracted from the refrigerant as it flows through the channel 570 and is transferred to coolant flowing through a channel 572 in the condenser 560. Refrigerant exits the channel 570, passes through the conduit 580 and then expansion valve 581 (which reduces the refrigerant pressure and temperature), and then enters evaporator 582. Heat from coolant 551 can cause evaporation of the heat transfer fluid in the evaporator 582. In some embodiments, the evaporator 582 can include one or more helical or curved tubes, tubes with fins, or other elements for transferring heat. Vapor from the evaporator 582 can be delivered through the conduit 590 back to compressor 591.

Warm coolant exiting the liquid-cooled condenser 560 at the channel 572 is pumped by pump 714 through liquid-to-air heat exchanger 561 and returns through conduits 562 and 563 to the condenser 560. A forced air device (e.g., a fan, a pump, etc.) can drive air through the heat exchanger 561 to exhaust collected heat into the surrounding environment.

In cooling and coasting operating states, a control valve 709 is shut so that all coolant exiting heat exchanger 561 flows through conduit 563 and back into condenser 560. In system heating state, the control valve 709 is partially of fully opened to allow some of the warm coolant exiting the heat exchanger 561 to enter the applicator 540. Coolant exiting through the control valve 709 and conduit 720 is replaced by an equal volume of colder coolant flowing into pump 714 through conduit 626. In another embodiment, the conduit 626 can draw coolant from mixing reservoir 522, and conduit 720 could empty into mixing reservoir 522.

An applicator circulation circuit 530 ("circuit 530") can deliver coolant from the mixing reservoir 522 to an applicator 540. A pump 601 can drive coolant 551 through a conduit 611 and into the mixing reservoir 522. The mixing reservoir 522 can also hold coolant from the conduit 625. A pump 640 can drive the fluid through the conduit 630 and the applicator 540. After coolant has passed through the applicator 540, the coolant can be delivered to the mixing reservoir 522 via the conduits 641, 625. Excess coolant can flow over an upper edge 700 of an open end 701 of the mixing reservoir 522. As such, the open end 701 can function as a passive leveling feature. At least a portion of the mixing reservoir 522 can be immersed in the coolant 551 to cool a wall 523 of the mixing reservoir 522. The configuration and components of the cooling system 544 can be selected based on desired cooling rates and thermal loading.

Figure 7:
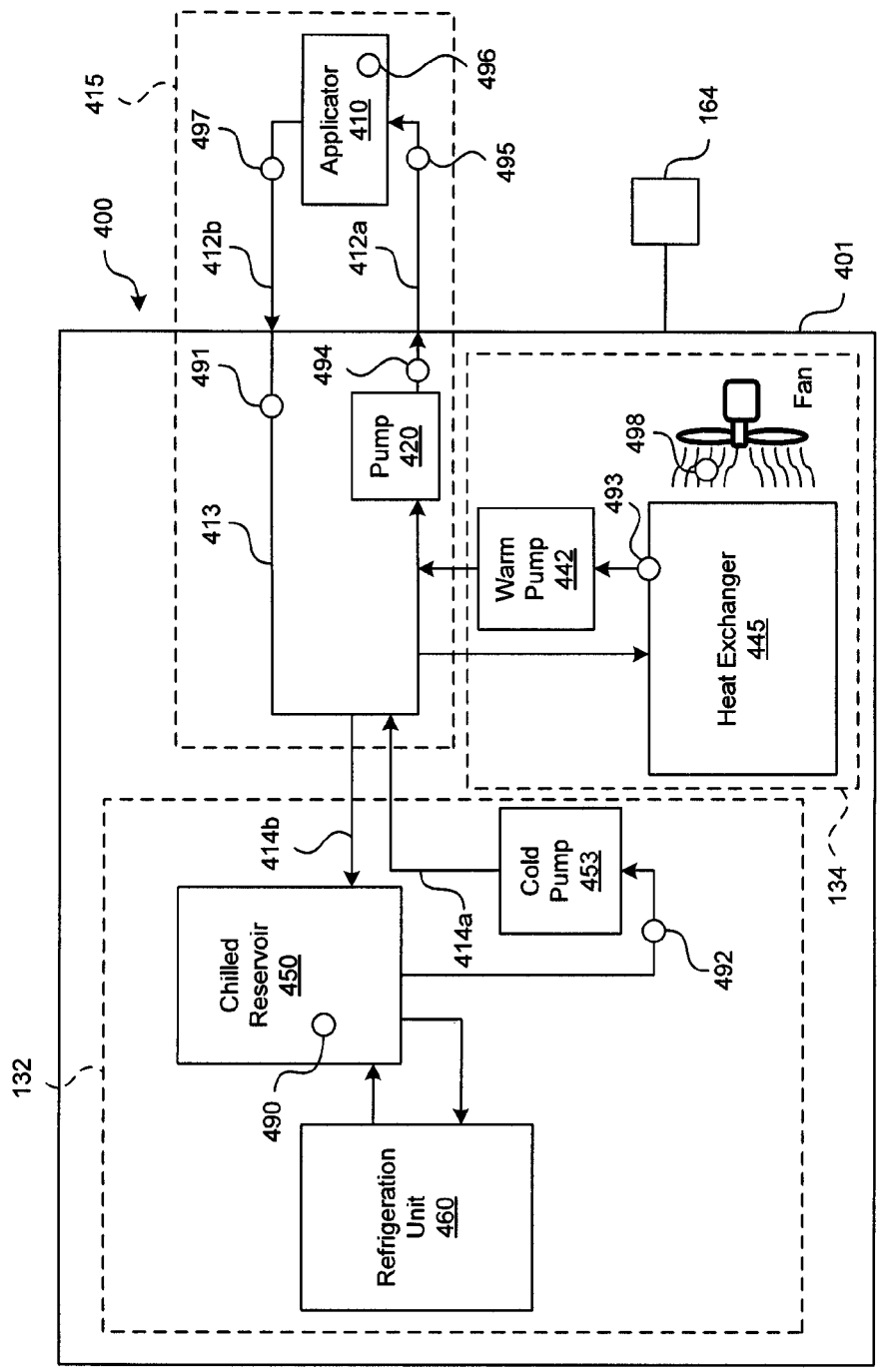
FIG. 7 is a schematic illustration of a treatment system in accordance with another embodiment.

FIG. 7 is a schematic illustration of a treatment system 400 that is generally similar to the treatment system 100 of FIGS. 1-3, except as detailed below. When the pump 453 is activated, chilled coolant is delivered through the conduit 414a and into the conduit 413. The conduit 413 can combine a stream of coolant from the conduit 414a with a stream of coolant from the applicator 410. The chiller fluidic circuit 132 can include a return conduit 414b that allows coolant to return to the chilled reservoir 450. The flow rate of coolant flowing through the return conduit 414b can be generally equal to the flow rate of coolant flowing through the supply conduit 414a. In some embodiments, the return conduit 414b allows equalization of pressures in the applicator circulation circuit 150 and the reservoir 450. A pressure differential, if any, can be dependent on, for example, the flow resistance of the conduit 414b. The internal flow area of the conduit 414b, length of the conduit 414b, and flow rate through the conduit 414b can be selected to keep the flow resistance at or below a desired level.

The volume of coolant contained in the applicator circulation circuit 415 of FIG. 7 can be substantially less than the volume of coolant in the applicator circulation circuit 150 of FIGS. 1 and 3. As a result, the applicator circulation circuit 415 of FIG. 7 can have a lower thermal mass than the applicator circulation circuit 150 of FIGS. 1 and 3, and the temperature of the coolant provided to the applicator 410 of FIG. 7 can be rapidly increased or decreased due to such low thermal mass. In some embodiments, the thermal mass of the coolant in the applicator circulation circuit 415 is equal to or less than about 20%, 30%, or 40% of the total thermal mass of coolant in the mixing reservoir 430 of FIG. 3 (e.g., when mixing reservoir 430 is completely filled with coolant).

A temperature sensor 490 can be used to detect the temperature of chilled coolant to control a cooling device in the form of refrigeration unit 460. The refrigeration unit 460 can have a simple off-on control routine consisting of fixed temperature set points for turning on and off. In other embodiments, the control can factor in anticipated cooling demands and drive the chilled reservoir to colder temperatures to increase the heat sinking capacity in anticipation of periods of particularly high peak heating loads. The heat removal set point for the refrigeration unit 460 may be selected based on, for example, a status of the applicator 410 and/or predicted cooling demand as determined by a combination of one or more temperature measurements. In some embodiments, the controller 164 can predict demand based on, for example, one or more of temperature output from the sensor 490 (including time history of temperature measured by sensor 490), ambient air temperature measured by sensor 497, and output from applicator sensor 496 (e.g., a sensor that outputs temperature readings, type of applicator, etc.), as well as other measurements and/or parameters. Such parameters can include, without limitation, progress/status of the treatment sequence, input from a user, and time remaining of treatment session.

With continued reference to FIG. 7, the sensor 496 can be a temperature sensor used to control the temperature of the applicator 410. If the measured temperature is higher than a target temperature, the pump 453 can be activated (or sped up) to deliver chilled coolant from the chilled reservoir 450 to the applicator circulation circuit 415. The chilled coolant reduces the temperature of coolant circulating in the applicator circulation circuit 415. If the measured temperature at the applicator 410 is slightly lower than desired, the pump 453 may be deactivated (or slowed down) to allow heat from the subject to slowly raise the temperature of the coolant circulating through the applicator circulation circuit 415. If the temperature at the applicator 410 is significantly colder than desired (e.g., when a treatment profile includes a ramp up in temperature), the pump 442 can be activated (or sped up) to deliver heated or warm coolant (e.g., coolant at or near ambient air temperature, or coolant at or near a refrigeration condenser temperature) to the applicator circulation circuit 415. In some embodiments, heat exchanger 445 is thermally linked with the heat rejection side of refrigeration unit 460, and the operation of refrigeration unit 460 can be cycled on when needed to elevate the temperature of coolant in heat exchanger 445 to temperatures above room temperature. The One or more variable speed device(s) (e.g., a variable speed refrigerant compressor, a variable speed condenser fan, etc.) can cooperate to provide a desired elevated temperature in heat exchanger 445 to increase the rate of heat removal from coolant in the chilled reservoir 450.

The controller 164 can operate based on a proportional-integral-differential (PID) algorithm based on a single temperature measurement, such as the temperature measurement from the temperature sensor 496. If the differential between the temperature of the subject contacting surface of the applicator 410 and the temperature measurement of sensor 495 and/or the temperature differential between the subject contacting surface of the applicator 410 and the measurement from the temperature sensor 494 are sufficiently small, the controller 164 can control the treatment system 400 based on only measurements from either sensor 494 or sensor 495. A PID control scheme employed based on one temperature sensor at or near the applicator 410 may be limited in accuracy and speed of response to external changes. To enhance performance, information can be factored into the control algorithms used to determine, for example, operation of the pumps (e.g., pumps 420, 442, 453). For example, the temperature of the coolant mixture near the inlet or outlet of pump 420 can be monitored by the sensor 494. The temperature difference between the measurements from sensor 494 and sensors 495 and 496 can be tracked, trended, and otherwise analyzed. A target temperature for the sensor 494 can be established based on, for example, the target temperature of the sensor 496, the stored information (such as the historic temperature different between the sensors 494, 496), etc. The feedback control scheme can also provide a feedback sensor reading at sensor 494 which responds to changes in flow speeds through cold pump 454 and/or warm pump 442.

The controller 164 can also control the treatment system 400 based on, for example, flow rates (e.g., mass flow rates, volume flow rates, etc.), energy relationships, energy equations, and the like. A feedback loop used in combination with, for example, mass flow rate, volume flow rate, and energy equations can control operation of pumps. By using this flow and energy information, the controller 164 can compensate for and respond with the appropriate adjustment to flow rates under a wider range of conditions. By measuring and factoring in additional temperature information, a feedback algorithm can be used to achieve stable and accurate control of the cooling applied to the target tissue. For example, the controller 164 can cycle the cooling device 360 to keep the chilled coolant in a target temperature range, although the temperature of the coolant would fluctuate within that target temperature range.

The temperature sensor 490 can be used to control refrigeration unit 460 using, for example, an ON/OFF control or a variable control. The status of reservoirs and the anticipated cooling demand can be determined by a combination of one or more of:

temperature readings from the sensor 490;
stored information (e.g., time history of temperature measured by sensors);
ambient temperature information from the sensor 498;
information about the applicator 410 (e.g., number of applicators, type of applicators, etc.) coupled to the control unit 401;
treatment information (e.g., progress/status of treatment setup sequence via user interface on the control unit 401); and
treatment session information (e.g., time remaining and details of progress/status of treatment cycle applied to applicator 410).

The pumps 420, 442, 453 can be gear pumps. The flow rates through each pump can be determined by the measured speed of the shaft and the known pump displacement per shaft revolution. When the flow rates are known, then the speeds needed to achieve a desired mixed fluid temperature at sensor 494 can be predicted.

Fluid streams combine where supply conduit 414a dumps into fluid conduit 413. The thermal energy of the combined streams can be generally equal to the combined thermal energy of the two contributing flow streams as described by the following equation:

$$[M_{414a} * C_{p\ Coolant} * T_{414a}] + [(M_{413} - M_{414b}) * C_{p\ coolant} * T_{491}] = [M_{420} * C_{p\ Coolant} * T_{494}]$$

Where
$M_{xxx}$=Mass flow rate of coolant through item xxx (e.g., $M_{414a}$=mass flow rate through conduit 414a,
$C_{p\ Coolant}$=Specific heat of coolant, and
$T_{xxx}$=Temperature at item or location xxx (e.g., $T_{491}$=temperature at sensor 491)

If the specific heat of the coolant is considered to be generally constant (e.g., ignoring relatively small changes of specific heat as a function of temperature), the specific heat can be cancelled from the above equation. The controller 164 can calculate the predicted thermal energy of the combined streams based on the above equation. The equation can be simplified. Substituting $M_{453}$ for both $M_{414a}$ and $M_{414b}$, and substituting $M_{420}$ for $M_{413}$ the equation can be simplified to:

$$[M_{453} * T_{414a}] + [(M_{420} - M_{453}) * T_{491}] = [M_{420} * T_{494}]$$

Then to:

$$T_{494} = (R) * (T_{492}) + (1-R) * (T_{491})$$

where R=Ratio of mass flow rates:$(M_{453})/(M_{420})$

If the density of coolant is approximated as a constant, then volume flow rates can be substituted for the mass flow rates because the coolant density constant can be cancelled out of all terms in the equation. The simplified equation is:

$$T_{494} = (R_v) * (T_{492}) + (1-R_v) * (T_{491})$$

where $R_v$=Ratio of volume flow rates:$(V_{453})/(V_{420})$

For a desired temperature $T_{494}$ and measured temperatures $T_{492}$ and $T_{491}$, the controller 164 can determine the corresponding flow rate ratio $R_v$. For a measured flow rate $(V_{420})$ through the pump 420 and applicator 410, the cold pump flow rate $(V_{453})$ can be calculated. The controller 164 can store various databases correlating flow rates to operational speeds of pumps. For example, the controller 164 can store pump flow rates and corresponding operational parameters for flow rates through the applicator 410. Based on a desired flow rate through the applicator 410, the controller 164 can determine appropriate operation of the pumps.

Figure 8:
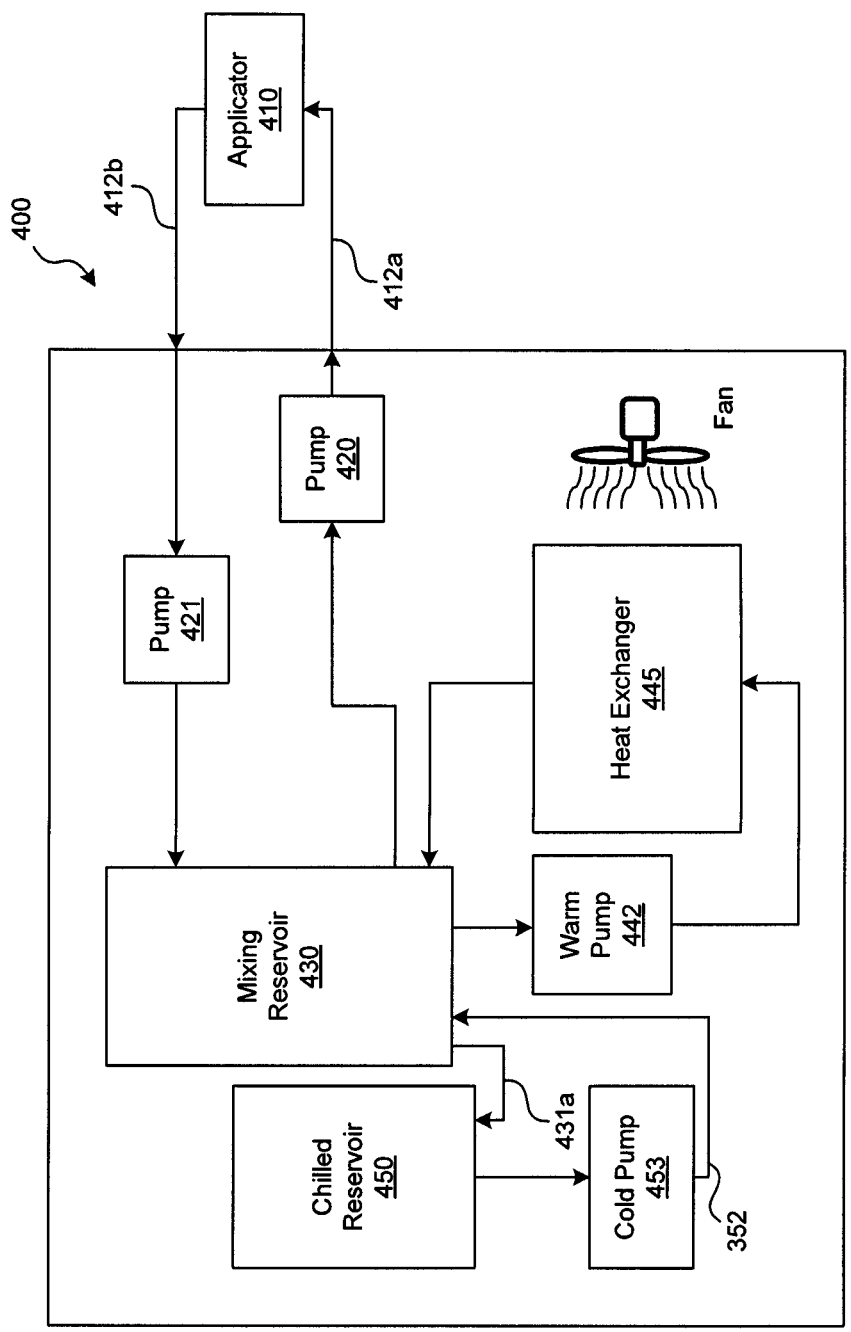
FIG. 8 is a schematic illustration of a treatment system in accordance with another embodiment.

FIG. 8 is a schematic illustration of a treatment system 400. The general principles described above in reference to FIGS. 1-3 apply to treatment system 400, except as detailed below. When the chilled or cold pump 453 is off, the flow conduit 431a allows the fluid levels in the chilled reservoir 450 and the mixing reservoir 430 to generally equalize. When the chilled pump 453 is on, the fluid level in the mixing reservoir 430 can begin to rise and produce a pressure differential proportional to the difference in the fluid height levels in the mixing and chilled reservoirs 430, 450. This pressure differential may create a return flow through the flow conduit 431a. If the mixing reservoir 430 has a sufficient holding capacity and if the flow conduit 431a provides a sufficiently low flow resistance, then a return flow rate to the chilled reservoir 450 can be substantially equivalent to the maximum flow rate through the conduit 352. As a result, the fluid levels between the mixing reservoir 430 and the chilled reservoir 450 can be generally equilibrated without relying on, for example, fluid level sensors. However, fluid level sensors can be used to monitor the coolant, if needed or desired.

The mixing reservoir 430 can be conveniently drained using the chilled reservoir 450. For example, the chilled reservoir 450 can be drained, which causes draining of the mixing reservoir 430. As the fluid level in the chilled reservoir 450 is lowered, coolant can flow from the mixing reservoir 430 into the chilled reservoir 450. Ultimately, all of the fluid can be drained via the chilled reservoir 450. In other embodiments, the conduit 431a can be connected to a drain.

Figure 9:
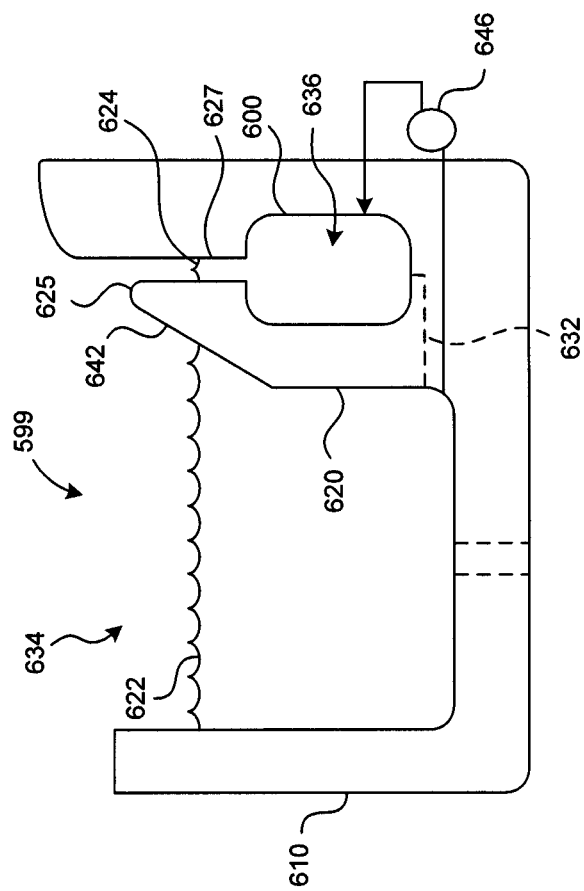
FIG. 9 is a schematic cross-sectional view of a structure including a mixing reservoir and a chilled fluid reservoir in accordance with one embodiment.

FIG. 9 is a schematic illustration of a structure 599 including a mixing reservoir 600 and a chilled reservoir 610 that share a common wall 620 to minimize or limit heat losses. The mixing reservoir 600 can have a holding capacity that is significantly less than the holding capacity of the chilled reservoir 450 of FIG. 3 because coolant levels 622, 624 can be automatically leveled. A fluid conduit 632 can fluidically couple the mixing reservoir 600 to the chilled reservoir 610. In some embodiments, the fluid conduit 632 is a passageway formed in the wall 620. In other embodiments, the fluid conduit 632 can be a hose or a tube extending between a chamber 634 of the chilled reservoir 610 and a chamber 636 of the mixing reservoir 600. The fluid conduit 632 can allow passive filling (or draining) of the mixing reservoir 600. The flow restriction provided by the fluid conduit 632 can be sufficient to minimize or limit significant unintentional interchange of fluid when transporting the structure 599.

A passive leveling device in the form of a spillway 642 allows excess coolant to flow from the mixing reservoir 600 to the chilled reservoir 610. When a pump 646 delivers an excess volume of coolant to the mixing reservoir 600, the coolant level 624 can rise to an upper edge 625 of the spillway 642, and additional volumes of coolant can flow down the spillway 642 and into the chamber 634. Although not illustrated, the mixing reservoir 600 can be in fluid communication with one or more applicators. Thus, the structure 599 can be incorporated into the treatment systems disclosed herein.

Figure 10:
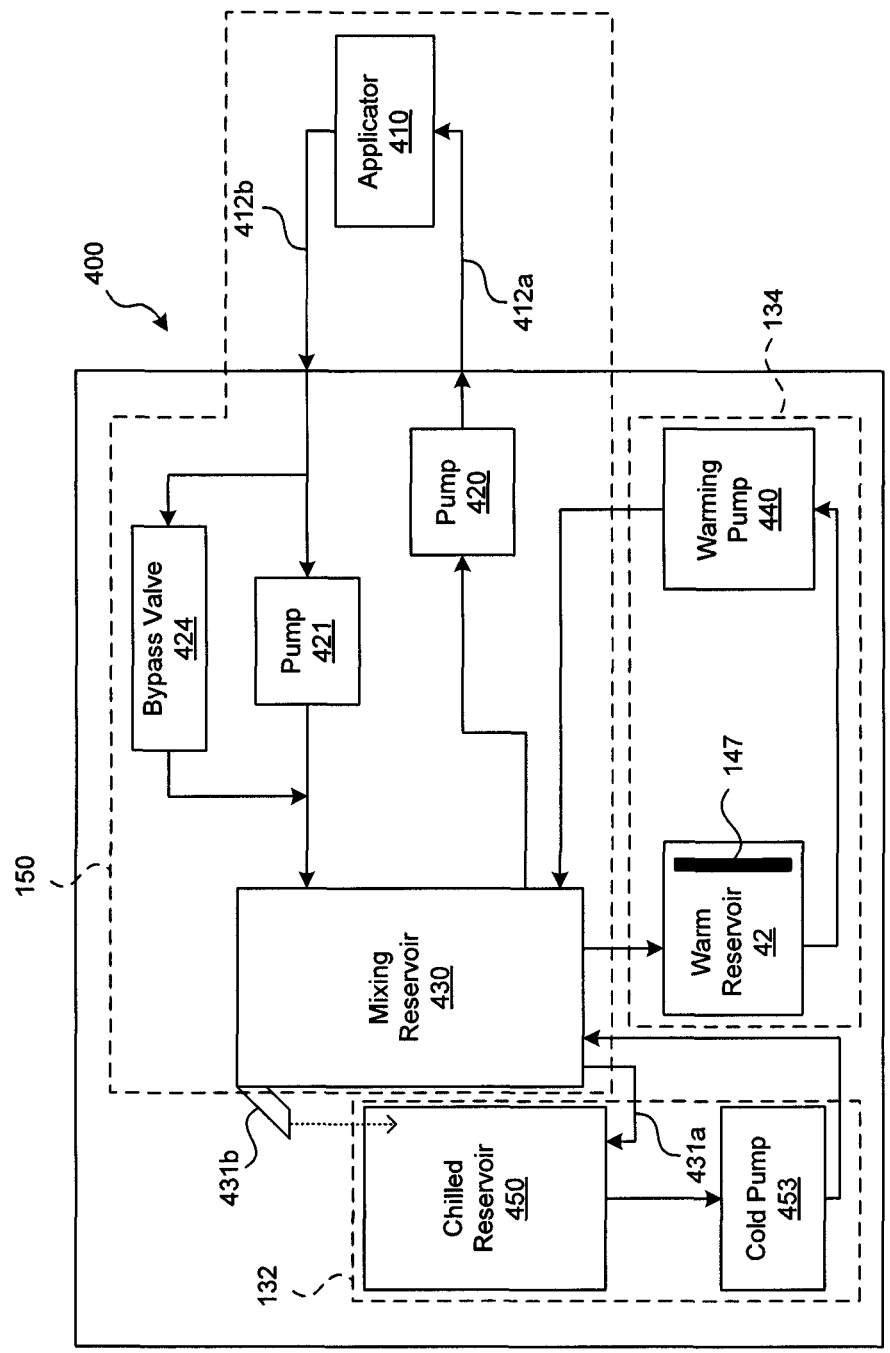
FIG. 10 is a schematic illustration of a treatment system with a bypass valve in accordance with one embodiment of the disclosure.

FIG. 10 is a schematic illustration of a treatment system 400 that includes a heater apparatus comprising a heater fluidic circuit 134 with a warm reservoir 441 with a heater 427. The pump 421 is capable of providing suction via the return conduit 412b so that the fluid pressure within the applicator 410 remains near atmospheric pressure (e.g., slightly under atmospheric pressure). The low pressure can be maintained to limit or prevent deformation of compliant components of the applicator 410 (e.g., a highly compliant vacuum cup). A valve, such as bypass valve 424, can be used to allow fluid flow around the pump 421, thereby extending the useful life of the pump 421. If the applicator 410 is capable of withstanding significant pressures (e.g., the applicator 410 includes a rigid vacuum cup), the bypass valve 424 can allow fluid flow around the pump 421, while the pump 420 drives the fluid through circulation circuit 150. The bypass valve 424 may be an active valve or a passive valve. Active valves can be solenoid driven valves, latching solenoid valves, or other types of valves driven from an open position to a closed position. Passive valves can include, without limitation, one-way valves, check valves, other types of valves that operate without active control.

Chilled reservoirs can use one or more phase change materials (PCM) to reduce or limit coolant volumes. A small amount of phase change material can replace a much larger amount of coolant. This reduction in coolant volumes can help reduce the time to cool the coolant within the chilled reservoir to reach a useful temperature range. For example, a chilled reservoir containing a small amount of coolant and a PCM with phase transition temperature of $-20°$ C. can be rapidly lowered from room temperature to a temperature of about $-15°$ C. Once the temperature of the chilled reservoir reaches the phase change temperature, the PCM's can absorb or "soak up" relatively large quantities of heat (when freezing) and release heat (while thawing) to generally dampen out the effects of large dynamic changes in the thermal load during, for example, temperature ramp-down, steady state operation, etc. In some embodiments, the PCM can be located within a primary liquid storage reservoir and can be encapsulated to prevent it from mixing with the liquid coolants.

PCMs can include, without limitation, hydrated inorganic salts, organic compounds (e.g., organic hydrocarbon blends, waxes, oils, etc.), or other substances that can store and release thermal energy during phase changes, such as melting and freezing. At least some PCMs have latent heat of fusion values that are significantly higher than the specific heat capacity of the associated liquid coolant. As a result, the PCMs (e.g., PCM-HS23N, MPCM-10D, etc.) can have a higher heat absorption capacity per unit volume than coolants. Inorganic salt PCMs can have latent heat of fusion of about 200 kJ/kg, whereas the organic hydrocarbons can have latent heat of fusion of about 150 kJ/kg. Specific gravity of inorganic salts can be about 1.2, whereas the specific gravity for organic hydrocarbons can be about 0.9. Other PCMs can have other properties. The compositions of PCMs can be selected such that the PCMs undergo a phase change at a specific temperature (or within a temperature range).

The PCM phase change temperature or temperature range can be selected to be near the chilled reservoir standby temperature such that the PCM absorbs thermal energy delivered into the chilled reservoir helping to maintain the reservoir temperature below the temperature of the coolant in the applicator circulation circuit. When the chilled reservoir coolant temperature is maintained below the temperature of the applicator circulation circuit, the treatment system can maintain a set point temperature of the applicator's cooling surface(s) as the surfaces are subjected to a heat flux. Advantageously, PCM can enable reduction of the holding capacity of the chilled reservoir. Reducing the volume and thermal mass of the chilled reservoir can reduce the cool-down time required for the cooling device to achieve a standby temperature after the system is provided with power. In some embodiments, the reduction in the cool-down time can be greater than about 30%. Other reductions of cool-down time can also be achieved.

A heat exchanger can be used to transfer heat from the PCM to coolant held in the chilled reservoir. FIG. 3 shows a heat exchanger 650 configured to transfer heat from coolant to the PCM 651. The PCM 651 can absorb significant amounts of thermal energy to reduce the holding capacity of the chilled reservoir 450. The configuration of heat exchanger 650 can be selected based on, for example, the desired surface area to volume ratio, available surface area for heat transfer, or the like. The surface area to volume ratio can define the surface area of a component containing the PCM to the volume of the component. For example, the component containing the PCM can be a tube. The surface area to volume ratio can be the outer surface area of the tube to the interior volume of the tube. The surface area to volume ratio can be increased to increase heat transfer rate between the PCM and the surrounding chilled coolant. Conversely, a lower surface area to volume ratio can be selected to reduce the heat transfer rate. In some embodiments, the heat exchanger 650 is a double pipe heat exchanger. The double pipe heat exchanger can include an inner pipe and an outer pipe. The inner pipe can contain the PCM. The outer pipe can surround the inner pipe and contain the chilled coolant. Thermal elements (e.g., fins) of the inner pipe can increase heat transfer. In some embodiments, the inner pipe can be a copper pipe with fins extending through a chamber between the inner pipe and the outer pipe. The chilled coolant can flow along inner pipe and the PCM can be held in the chamber. In other embodiments, the chilled coolant flows along the chamber while the PCM is contained in the inner pipe.

Figure 11:
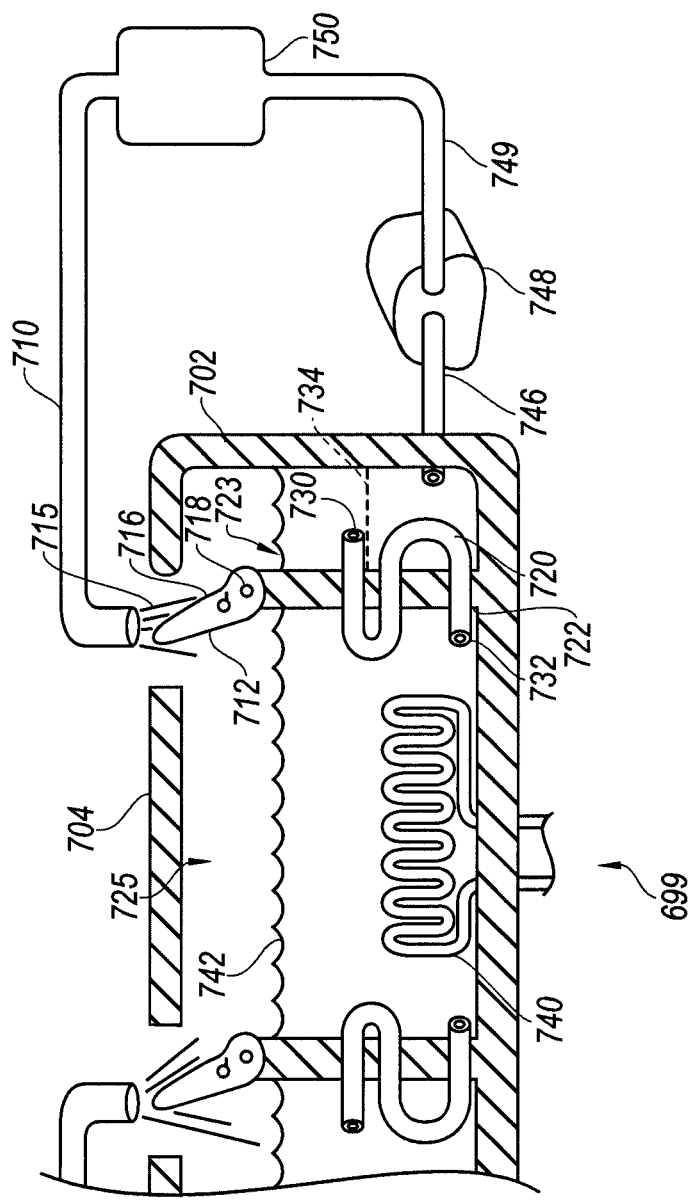
FIG. 11 is a partial cross-sectional view of a treatment system in accordance with one embodiment of the disclosure.

FIG. 11 is a schematic illustration of a structure 699 including a mixing reservoir 702 and a chilled coolant reservoir 704 ("chilled reservoir 704"). The mixing reservoir 702 can receive coolant from a return conduit 710. A diverter or valve device 712 (e.g., a diverter valve, a T-valve, or the like) can selectively deliver warm coolant 715 to the mixing reservoir 702 and/or chilled reservoir 704. In the illustrated embodiment, the valve device 712 has a valve member 716 rotatable about a pin 718. An S-shaped flow conduit 720 is positioned in a sidewall 722 and extends between a chamber 723 of the mixing reservoir 702 and a chamber 725 of the chilled reservoir 704. In other embodiments, the flow conduit 720 has other configurations. An inlet 730 can be higher than an outlet 732 to maintain a minimum volume or level (represented by dash line 734) of coolant in the mixing reservoir 702. A cooling device 740 is in thermal communication with the coolant 742 and can operate on a refrigeration system cycle.

In operation, coolant can flow out of the mixing chamber 723 via the conduit 746. A drive device in the form of a pump 748 causes the fluid to flow through a supply conduit 749 to an applicator 750. The applicator 750 can transfer heat from the subject to the coolant. The coolant can be delivered to a return conduit 710 which outputs the coolant towards the valve device 712, which can direct the coolant to the chilled reservoir 704 and/or mixing reservoir 702. To reduce the temperature of the coolant in the mixing reservoir 702, the coolant can be delivered to the chilled reservoir 704. As the returning fluid is delivered to chilled reservoir 704 the fluid level in mixing reservoir 702 drops and the fluid level in chilled reservoir 704 rises. The level imbalance drives cold fluid from chilled reservoir 704 through conduit 720 into mixing reservoir 702 where it mixes with and cools the liquid in the mixing reservoir. The cooling device 740 can reduce the temperature of coolant 742 in chilled reservoir 725.

To allow heat transferred from applicator 750 to cause the temperature of mixing reservoir 702 to rise, valve device 712 can direct all of the fluid returning from applicator 750 back into mixing reservoir 702. In this case the flow rate returning to mixing reservoir 702 through conduit 746 matches the flow rate exiting through conduit 746 and the fluid levels in the mixing reservoir 702 and chilled reservoir 704 can generally equilibrate. Once the fluid levels equilibrate, fluid level imbalances no longer drive flow of cold fluid from chilled reservoir 704 through conduit 720 into mixing reservoir 702. In some embodiments the diverter or valve device 712 can be adjusted to allow a fraction of the return flow rate to be diverted to mixing reservoir 702, in other embodiments flow is diverted fully one direction or the other and control is achieved by modulating valve device 712 back and forth between mixing reservoir 702 and chilled reservoir 704.

Figure 12:
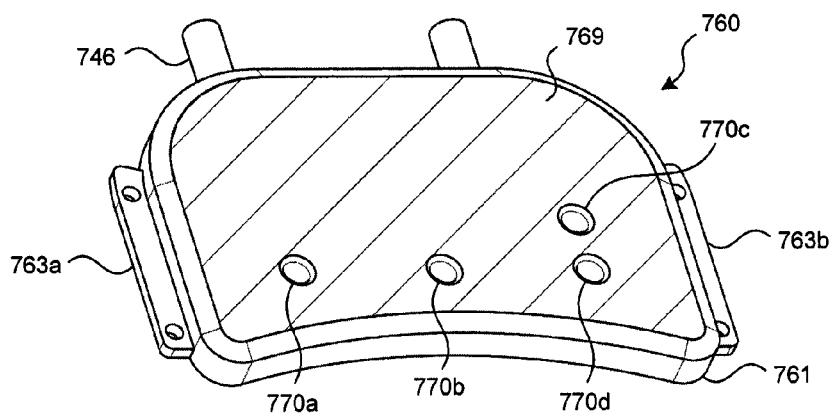
FIG. 12 is a top, front, and left side view of a heat exchanger element in accordance with one embodiment of the disclosure.
Figure 13:
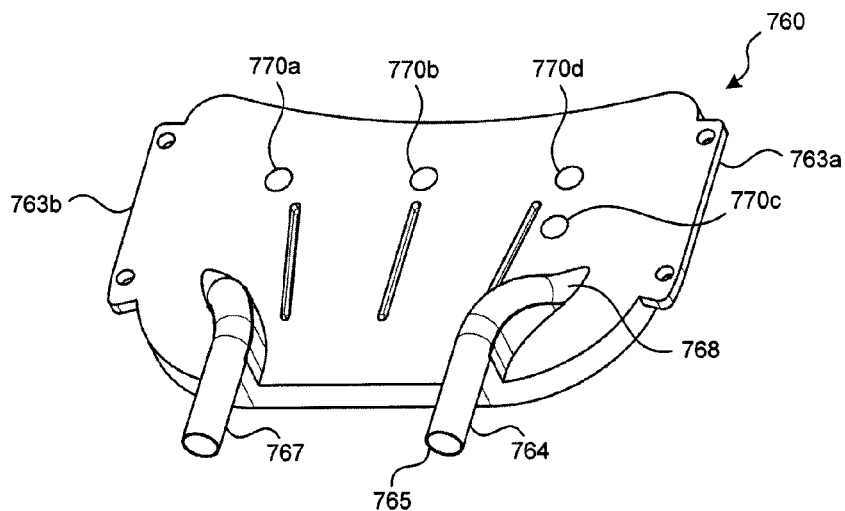
FIG. 13 is a bottom, back, and right side view of a heat exchanger element of FIG. 12.
Figure 14:
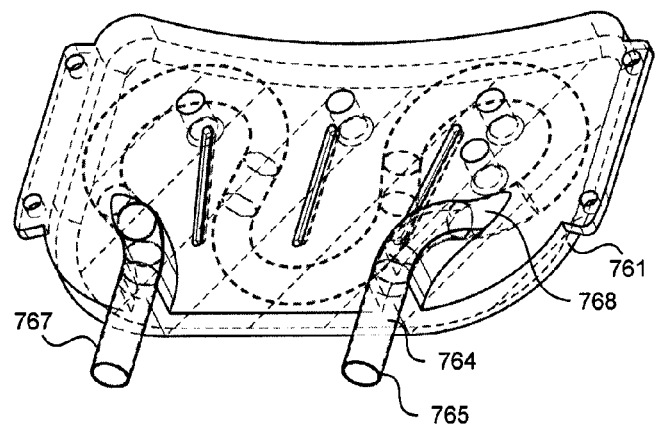
FIG. 14 is a schematic illustration of internal components of the heat exchanger element of FIG. 12.

FIG. 12 is a front side isometric view of a heat exchanger element 760 in accordance with one embodiment of the disclosure. FIG. 13 is a back side isometric view of the heat exchanger element 760. The heat exchanger element 760 can be incorporated into a wide range of different types of applicators, including the applicator 410 discussed in connection with FIGS. 1-5. The heat exchanger element 760 can include a main body 761 with mounting features 763 (shown individually as 763a, 763b) to couple to the heat exchanger element 760 to a cup or a housing of an applicator. As shown in FIG. 14, a conduit 764 has an inlet 765 for receiving coolant, an output 767 for outputting coolant, and a main body 768 located within the main body 761. Openings 770 (shown individually as 770a, 770b, 770d, 770c in FIG. 13) allow access to the front side. One or more wires can extend to the opening 770 to sensors or other components on the front side of the heat exchanger element 760.

FIG. 14 shows the tubular main body 768. The tubular main body 768 can be an extruded tube or other tubular conduit through which a coolant can flow. Advantageously, the tubular main body 768 can be formed (e.g., bent) into a wide range of different shapes. Additionally, the tubular main body 768 can reduce or eliminate the occurrence of leakage. The main body 768 can be made of a high heat transfer material including, without limitation, copper, aluminum, stainless steel, or other materials suitable for transferring heat between the coolant and the front surface 769 (FIG. 12). In other embodiments, the conduit 764 can comprise multiple tubular members that are welded together. In one embodiment, conduit 764 is made of stainless steel and the remainder of heat exchanger element 760 is made of cast aluminum.

Figure 15:
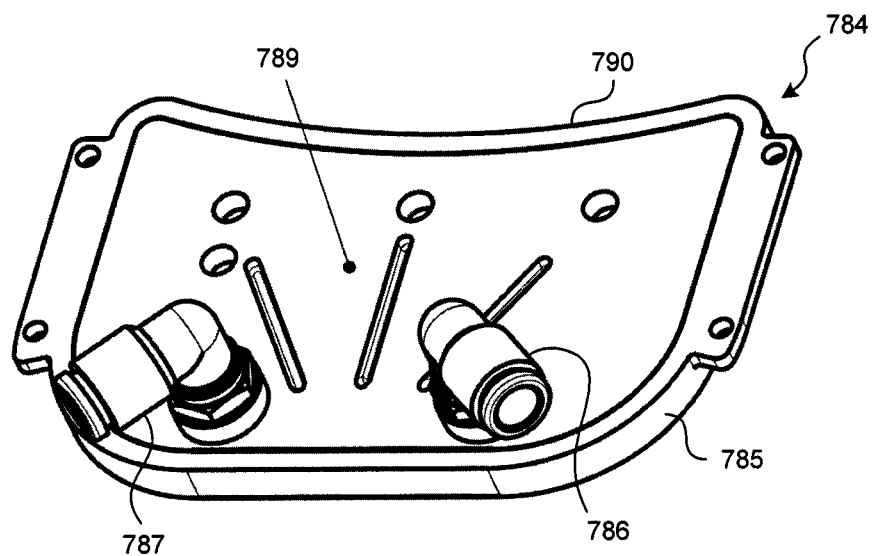
FIG. 15 is a bottom, back, and right side view of a heat exchanger element in accordance with an embodiment of the disclosure.
Figure 16:
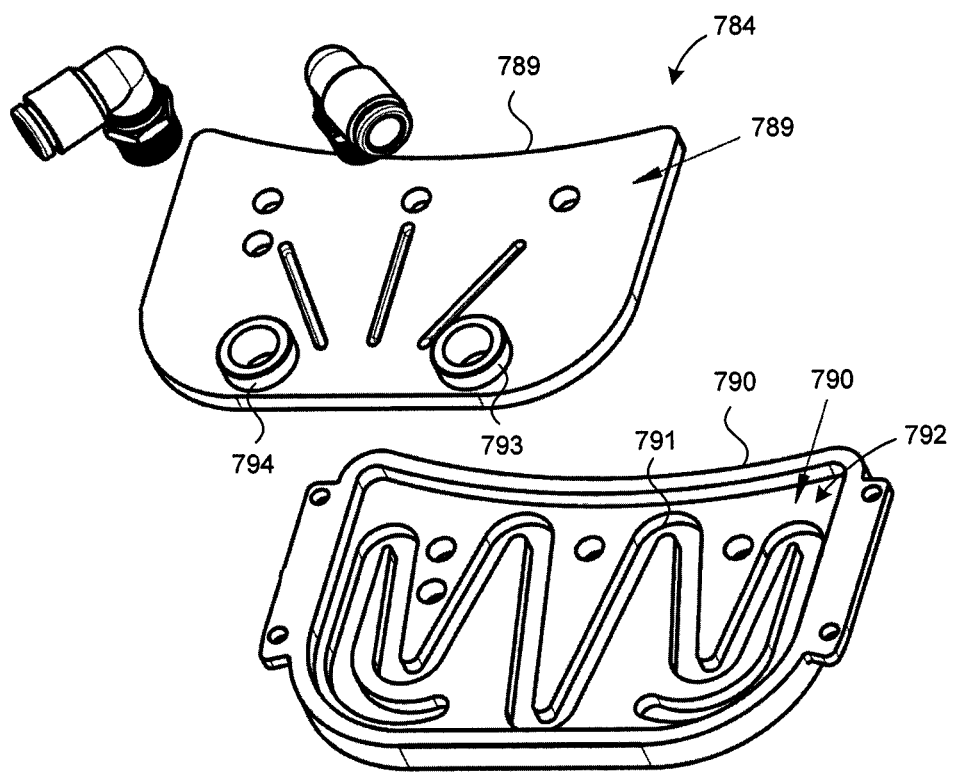
FIG. 16 is an exploded view of the heat exchanger element of FIG. 15.

FIG. 15 is a back side isometric view of a heat exchanger element 784. FIG. 16 is an isometric exploded view of the heat exchanger element 784. The heat exchanger element 784 includes a main body 785 and an inlet 786 and an outlet 787. The heat exchanger 784 includes a back plate 789 and a front plate 790. The front plate 790 includes a passageway or channel 791 that defines a fluid path for heat transfer fluid. In another embodiment, the passageway could be formed instead or in addition in back plate 789. The back plate 789 can be positioned in a recessed region 792 and attached to front plate 790 (e.g., welded, brazed, adhesively bonded, etc.) such that the back plate 789 and front plate 790 seal the channel 791. To circulate fluid through the heat exchanger 784, a supply conduit can be coupled to the inlet 786. A return line can be coupled to the outlet 787.

The heat exchanger element 760 of FIGS. 12-14 and the heat exchanger element 784 of FIGS. 15 and 16 can be used in the applicators disclosed herein. For example, the heat exchanger elements 168 of FIG. 2 can be replaced with the heat exchanger element 760 or heat exchanger element 784.

In some examples, a cryoprotectant is used with the treatment systems and applicators disclosed herein to, among other advantages, assist in preventing freezing of non lipid-rich tissue (e.g., dermal tissue) during treatment as is described in commonly-assigned U.S. Patent Publication No. 2007/0255362. Temperature or heat flux measurements can indicate other changes or anomalies that can occur during treatment administration. For example, an increase in temperature detected at an applicator heat exchanging element 168 can indicate a freezing event at the skin or underlying tissue (i.e., dermal tissue). The system can be programmed to detect and respond to such temperature or heat flux changes, responding, for example, by changing from a cooling mode to a heating mode. An increase in temperature at the applicator can also indicate movement associated with the applicator, causing the applicator to contact a warmer area of the skin, for example. Methods and systems for collection of feedback data and monitoring of temperature measurements are described in commonly assigned U.S. Pat. No. 8,285,390.

The treatment systems and methods disclosed herein can be used to achieve a wide range of different treatment profiles, includes those disclosed in U.S. Patent Publication No. 2009/0018623 entitled "SYSTEM FOR TREATING LIPID-RICH REGIONS. Thus, temperatures, ramp characteristics (e.g., rate, time, shape, starting temperature, and ending temperature, etc.), dwell characteristics, etc. can be the as or similar to those disclosed in U.S. Patent Publication No. 2009/0018623.

3. Suitable Computing Environments

Figure 17:
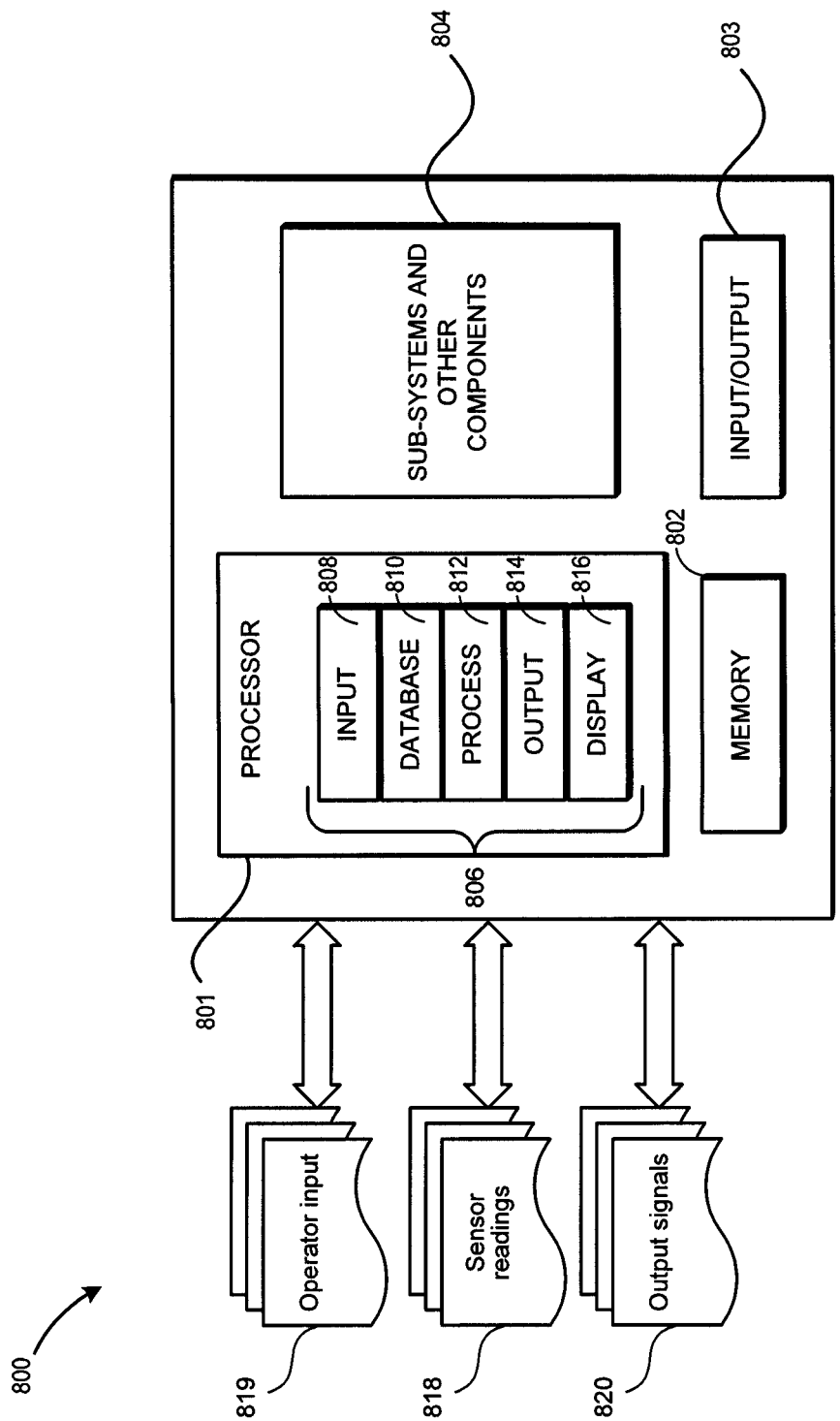
FIG. 17 is a schematic block diagram illustrating computing system software modules and subcomponents of a controller in accordance with an embodiment of the disclosure.

FIG. 17 is a schematic block diagram illustrating subcomponents of a computing device 800 in accordance with an embodiment of the disclosure. The computing device 800 can include a processor 801, a memory 802 (e.g., SRAM, DRAM, flash, or other memory devices), input/output devices 803, and/or subsystems and other components 804. The computing device 800 can perform any of a wide variety of computing processing, storage, sensing, imaging, and/or other functions. Components of the computing device 800 may be housed in a single unit or distributed over multiple, interconnected units (e.g., though a communications network). The components of the computing device 800 can accordingly include local and/or remote memory storage devices and any of a wide variety of computer-readable media.

As illustrated in FIG. 17, the processor 801 can include a plurality of functional modules 806, such as software modules, for execution by the processor 801. The various implementations of source code (i.e., in a conventional programming language) can be stored on a computer-readable storage medium or can be embodied on a transmission medium in a carrier wave. The modules 806 of the processor can include an input module 808, a database module 810, a process module 812, an output module 814, and, optionally, a display module 816.

In operation, the input module 808 accepts an operator input 819 via a control, and communicates the accepted information or selections to other components for further processing. The database module 810 organizes records, including patient records, treatment data sets, treatment profiles and operating records and other operator activities, and facilitates storing and retrieving of these records to and from a data storage device (e.g., internal memory 802, an external database, etc.). Any type of database organization can be utilized, including a flat file system, hierarchical database, relational database, distributed database, etc.

In the illustrated example, the process module 812 can generate control variables based on sensor readings 818 from sensors (e.g., the temperature measurement sensors 490, 492, 493, 494 of FIG. 7) and/or other data sources, and the output module 814 can communicate operator input to external computing devices and control variables to the controller 164 (FIG. 1). The display module 816 can be configured to convert and transmit processing parameters, sensor readings 818, output signals 820, input data, treatment profiles and prescribed operational parameters through one or more connected display devices, such as a display screen, printer, speaker system, etc. A suitable display module 816 may include a video driver that enables the controller 164 to display the sensor readings 818 or other status of treatment progression on the output device (e.g., a screen of the controller 164).

In various embodiments, the processor 801 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 802 can be standard memory, secure memory, or a combination of both memory types. By employing a secure processor and/or secure memory, the system can ensure that data and instructions are both highly secure and sensitive operations such as decryption are shielded from observation.

Suitable computing environments and other computing devices and user interfaces are described in commonly assigned U.S. Pat. No. 8,275,442, entitled "TREATMENT PLANNING SYSTEMS AND METHODS FOR BODY CONTOURING APPLICATIONS," which is incorporated herein in its entirety by reference.

4. Applicators

The treatment systems disclosed herein can be used with different types of applicators. Various types of applicators may be applied during treatment, such as a vacuum applicator, a belt applicator, a compliant applicator with a flexible and/or elastic heat exchange envelope (any of which may be used in combination with a massage or vibrating capability), and so forth. Each applicator may be designed to treat identified portions of the patient's body, such as chin, cheeks, arms, pectoral areas, thighs, calves, buttocks, abdomen, "love handles", back, and so forth. For example, the vacuum applicator may be applied at the back region, and the belt applicator can be applied around the thigh region, either with or without massage or vibration. Exemplary applicators and their configurations usable or adaptable for use with the treatment systems disclosed herein variously are described in, e.g., commonly assigned U.S. Pat. No. 7,854,754 and U.S. Patent Publication Nos. 2008/0077201, 2008/0077211, 2008/0287839, 2011/0238050 and 2011/0238051. In further embodiments, the treatment systems may also include a patient protection device (not shown) incorporated into or configured for use with the applicator 105 to prevent directed contact between the applicator and a patient's skin and thereby reducing the likelihood of cross-contamination between patients, minimizing cleaning requirements for the applicator. The patient protection device may also include or incorporate various storage, computing, and communications devices, such as a radio frequency identification (RFID) component, allowing for example, use to be monitored and/or metered. Exemplary patient protection devices are described in commonly assigned U.S. Patent Publication No. 2008/0077201.

5. Conclusion

From the foregoing, it will be appreciated that specific embodiments of the invention have been described herein for purposes of illustration, but well-known structures and functions have not been shown or described in detail to avoid unnecessarily obscuring the description of at least some embodiments of the invention. Where the context permits, singular or plural terms may also include the plural or singular term, respectively. Unless the word "or" is associated with an express clause indicating that the word should be limited to mean only a single item exclusive from the other items in reference to a list of two or more items, then the use of "or" in such a list shall be interpreted as including (a) any single item in the list, (b) all of the items in the list, or (c) any combination of the items in the list. The singular forms "a," "an," and "the" include plural referents unless the context clearly indicates otherwise. Thus, for example, reference to "a sensor" refers to one or more sensors, such as two or more sensors, three or more sensors, or four or more sensors.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A treatment system for cooling subcutaneous lipid-rich cells in a subject, comprising:
    an applicator configured to be in thermal communication with skin of the subject;
    a control unit having a cooling state and a heating state, the control unit including
        an applicator circulation circuit including a supply end in fluid communication with the applicator and a return end in fluid communication with the applicator, the applicator circulation circuit defining a flow path extending between the supply end and the return end and along which coolant flows to deliver coolant to the applicator,
        a chiller apparatus configured to chill coolant from the applicator circulation circuit, the chiller apparatus is configured to deliver chilled coolant to the applicator circulation circuit to reduce a temperature of coolant in the applicator circulation circuit from room temperature to a temperature less than 0° C. while chilled coolant in the chiller apparatus is maintained at a temperature less than 0° C. when the control unit is in the cooling state, and
        a heater apparatus configured to deliver heated coolant to the applicator circulation circuit to raise the temperature of the coolant in the applicator circulation circuit when the control unit is in the heating state;
    a controller having instructions that, when executed, causes the chiller apparatus to deliver chilled coolant to the applicator circulation circuit such that the coolant cools the applicator enough to keep the subcutaneous lipid-rich cells at or below 0° C. for a sufficient length of time to disrupt target subcutaneous lipid-rich cells; and
    a mixing reservoir along the flow path and configured to hold a sufficient volume of the coolant for cooling the applicator such that the applicator cools target subcutaneous lipid-rich cells to a temperature lower than 0° C.,
    wherein the chiller apparatus includes a chilled reservoir configured to hold a sufficient volume of pre-chilled coolant for mixing with and cooling the coolant held in the mixing reservoir to a temperature lower than 0° C.

2. The treatment system of claim 1 wherein the chiller apparatus includes a chiller fluidic circuit configured to hold a volume of chilled coolant and deliver chilled coolant to the applicator circulation circuit to reduce the temperature of coolant that is delivered to the applicator by at least about 20° C. in less than about 5 minutes.

3. The treatment system of claim 1 wherein the chiller apparatus includes a chiller fluidic circuit that receives coolant from the applicator circulation circuit and delivers chilled coolant to the applicator circulation circuit while coolant flows continuously along the flow path of the applicator circulation circuit.

4. The treatment system of claim 1 wherein the chiller apparatus includes a cooling device, wherein the chilled reservoir receives coolant from the applicator circulation circuit, and the cooling device removes heat from coolant contained in the chilled reservoir.

5. The treatment system of claim 1 wherein the applicator circulation circuit defines a primary loop, a chiller fluidic circuit of the chiller apparatus defines a first secondary loop, and a heater fluidic circuit of the heater apparatus defines a second secondary loop.

6. The treatment system of claim 1 wherein the chiller apparatus and the heater apparatus are configured to independently deliver the chilled coolant and heated coolant, respectively, to the applicator circulation circuit.

7. The treatment system of claim 1, further comprising a passive fluid leveling element that delivers coolant from the applicator circulation circuit to the chiller apparatus.

8. The treatment system of claim 7 wherein the passive fluid leveling element allows coolant to flow from the applicator circulation circuit to the chiller apparatus when a volume of the coolant in the applicator circulation circuit is at or above a limit volume.

9. The treatment system of claim 7 wherein the passive fluid leveling element includes a spillway that allows coolant to flow from the mixing reservoir to the chiller apparatus.

10. The treatment system of claim 7 wherein the passive fluid leveling element includes a conduit with one end fluidically coupled to the mixing reservoir and another end fluidically coupled to the chilled reservoir.

11. The treatment system of claim 10 wherein the conduit allows a level of chilled coolant in the chilled reservoir to generally equilibrate with a level of coolant in the mixing reservoir.

12. The treatment system of claim 1 wherein the mixing reservoir is configured to accept chilled coolant from the chiller apparatus and warm coolant from the applicator, the appilcator circulation circuit including a return conduit fluidically coupling an outlet of the applicator to the mixing reservoir, and a delivery conduit fluidically coupling the mixing reservoir to an inlet of the applicator.

13. The treatment system of claim 1, wherein the controller is in communication with the chiller apparatus and the heater apparatus, the controller containing instructions that, when executed, causes the controller to:
    command the chiller apparatus to deliver the chilled coolant to the applicator circulation circuit to lower a temperature of the coolant delivered to the applicator; and
    command the heater apparatus to deliver the heated coolant to the applicator circulation circuit to raise a temperature of the coolant delivered to the applicator.

14. The treatment system of claim 1 wherein the chiller apparatus includes a cold pump operative to direct the chilled coolant into the applicator circulation circuit, and wherein the heater apparatus includes a warm pump operative to direct the heated coolant into the applicator circulation circuit.

15. The treatment system of claim 1 wherein the applicator has a heat exchanger element configured to transfer heat from the subcutaneous lipid-rich cells of the subject to coolant in the applicator to affect the subcutaneous lipid-rich cells.

16. The treatment system of claim 1, further comprising a temperature monitoring device communicatively coupled to the controller, the controller containing instructions for commanding the chiller apparatus to deliver chilled coolant the applicator circulation circuit based, at least in part, on one or more signals from the temperature monitoring device.

17. The treatment system of claim 1, further comprising a temperature monitoring device communicatively coupled to the controller, the controller contains containing instructions for commanding the heater apparatus to deliver heated coolant into the applicator circulation circuit based, at least in part, on one or more signals from the temperature monitoring device.

18. The treatment system of claim 1 wherein the heater apparatus includes a heat exchanger that heats coolant from the applicator circulation circuit by extracting heat from air.

19. The treatment system of claim 1 wherein the control unit is configured to deliver the coolant at a temperature lower than the subject's skin temperature when the subject's skin temperature is equal to or lower than about −5° C.

20. The treatment system of claim 1 wherein the applicator includes a heat exchanger element having a heat exchanging body and a tubular member positioned within the heat exchanging body such that coolant flowing through the tubular member absorbs the heat transferred from the subject to the heat exchanging body.

21. The treatment system of claim 1 wherein the control unit is configured to deliver the coolant, which is at a temperature lower than about −5° C., from the chiller apparatus to the applicator.

22. A treatment system for cooling subcutaneous lipid-rich cells in a subject, the treatment system comprising:
an applicator configured to be in thermal communication the subject's skin;
a control unit having a cooling state and a heating state, the control unit including
an applicator circulation circuit including
a supply end in fluid communication with the applicator,
a return end in fluid communication with the applicator, and
a mixing reservoir positioned along a flow path of the applicator circulation circuit, the flow path extending between the supply end and the return end,
a chiller apparatus fluidically coupled to the applicator circulation circuit, the chiller apparatus including a chilled reservoir configured to hold a volume of pre-chilled coolant at a standby temperature that is lower than 0° C.;
a controller in communication with the control unit and the chiller apparatus, the controller containing instructions that, when executed, causes the controller to:
command the chiller apparatus to deliver chilled coolant from the chilled reservoir to the mixing reservoir to lower a temperature of coolant contained in the mixing reservoir to a temperature lower than 0° C., and
command the applicator circulation circuit to deliver the coolant cooled to a temperature lower than 0° C. from the mixing reservoir to the applicator such that the applicator cools target subcutaneous lipid-rich cells of the subject to a temperature lower than 0° C.; and
command the chiller apparatus to deliver chilled coolant to the applicator circulation circuit to cool the coolant in the applicator circulation circuit to keep the target subcutaneous lipid-rich cells at or below 0° C. for a sufficient length of time to disrupt the target subcutaneous lipid-rich cells.

23. The treatment system of claim 22 wherein the controller contains instructions to cause the chiller apparatus to continuously or periodically deliver the chilled coolant to the mixing reservoir to keep coolant flowing through the applicator at a temperature lower than about −5° C.

24. The treatment system of claim 22 wherein the controller contains instructions that, when executed, cause the chiller apparatus to deliver the chilled coolant to the applicator circulation circuit to reduce the temperature of the coolant delivered to the applicator from room temperature to a temperature less than about 0° C. while the chilled coolant in the chiller apparatus is maintained at a temperature lower than about 0° C.

25. The treatment system of claim 22 wherein the mixing reservoir is configured to hold a volume of the chilled coolant having a thermal mass equal to or less than about 70% of a total mass of the applicator circulation circuit.

26. The treatment system of claim 22 wherein the control unit is configured to deliver the coolant, which is at a temperature lower than about −5° C., to the applicator.

27. The treatment system of claim 22, further comprising a temperature monitoring device, the controller being communicatively coupled to the temperature monitoring device and containing instructions for commanding the chiller apparatus to deliver chilled to coolant the applicator circulation circuit based, at least in part, on one or more signals from the temperature monitoring device so to disrupt the target subcutaneous lipid-rich cells.

28. A treatment system for cooling subcutaneous lipid-rich cells in a subject, the treatment system comprising:
an applicator configured to be in thermal communication the subject's skin and including at least one temperature sensor,
a control unit having a cooling state and a heating state, the control unit including
an applicator circulation circuit including
a supply end in fluid communication with the applicator,
a return end in fluid communication with the applicator, and
a mixing reservoir positioned along a flow path of the applicator circulation circuit, the flow path extending between the supply end and the return end,
a chiller apparatus fluidically coupled to the applicator circulation circuit, the chiller apparatus including a chilled reservoir configured to hold a volume of pre-chilled coolant at a standby temperature that is lower than 0° C.;
a controller in communication with the at least one temperature sensor and the chiller apparatus, the controller having instructions that, when executed, causes the controller to
command the chiller apparatus to deliver chilled coolant from the chilled reservoir to the mixing reservoir to lower a temperature of coolant contained in the mixing reservoir to a temperature lower than 0° C., and command the control unit based on a temperature measurement from the at least one temperature sensor to deliver the coolant, which is at a temperature lower than 0° C., to the applicator such that the applicator cools target subcutaneous lipid-rich cells of the subject to a temperature lower than 0° C. for a sufficient length of time to disrupt the target subcutaneous lipid-rich cells.

29. The treatment system of claim 28, wherein the applicator includes at least one heat exchanger element configured to cool the subject's skin while the at least one temperature sensor provides temperature measurements.

* * * * *